United States Patent [19]

Gelfand et al.

[11] Patent Number: 5,310,652
[45] Date of Patent: May 10, 1994

[54] REVERSE TRANSCRIPTION WITH THERMOSTABLE DNA POLYMERASE-HIGH TEMPERATURE REVERSE TRANSCRIPTION

[75] Inventors: David H. Gelfand, Oakland; Thomas W. Myers, Emeryville, both of Calif.

[73] Assignee: Hoffmann-La Roche Inc., Nutley, N.J.

[21] Appl. No.: 82,182

[22] Filed: Jun. 24, 1993

Related U.S. Application Data

[63] Continuation of Ser. No. 746,121, Aug. 15, 1991, abandoned, and a continuation-in-part of Ser. No. 455,967, Dec. 22, 1989, abandoned, and a continuation-in-part of Ser. No. 609,157, Nov. 2, 1990, abandoned, which is a continuation-in-part of Ser. No. 557,517, Jul. 24, 1990, abandoned, said Ser. No. 746,121, is a continuation-in-part of Ser. No. 585,471, Sep. 20, 1990, abandoned, which is a continuation-in-part of Ser. No. 455,611, Dec. 22, 1989, said Ser. No. 455,967, is a continuation-in-part of Ser. No. 143,441, Jan. 12, 1988, which is a continuation-in-part of Ser. No. 63,509, Jun. 17, 1987, Pat. No. 4,889,818, which is a continuation-in-part of Ser. No. 899,241, Aug. 22, 1986, abandoned.

[51] Int. Cl.$^5$ .................. C12P 19/34; C12Q 1/68; C07H 5/04; C07H 15/12
[52] U.S. Cl. .................. 435/6; 435/91; 435/7.91; 536/18.7; 536/25.6; 935/77; 935/78
[58] Field of Search .................. 435/6, 91, 227, 7.91; 436/21; 536/18.7, 25.6; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 5,035,996 | 6/1991 | Hartley | 435/6 |

FOREIGN PATENT DOCUMENTS

| | | |
|---|---|---|
| 0258017 | 3/1988 | European Pat. Off. |
| 359006 | 3/1990 | European Pat. Off. |

OTHER PUBLICATIONS

Brown, Basic Principles in Nucleic Acid Chemistry 2:41-45, New York, Academic Press.
Houdebine, 1976, "Synthesis of DNA Complementary to the mRNAs for Milk Proteins by *E. coli* DNA Polymerase I" Nucleic Acids Research 3(3):615-630.
Karkas et al., 1972, "Action of DNA Polymerase I of *Escherischia coli* with DNA-RNA Hybrids as Templates" Proc. Natl. Acad. Sci. USA 69(2):398-402.
"Metal Ions in Genetic Information Transfer" in Advances in Inorganic Biochemistry vol. 3, pp. 26-29, 32-35, and 42-46 published by Elsevier North Holland Inc. New York, New York Eds. Eichorn, Gunther, Louis and Marzill, Luigi, 1981.
Mizutani and Temin, 1976, "Incorporation of Noncomplementary Nucleotides at High Frequencies by Ribodeoxyvirus DNA Polymerases and *Escherichia coli* DNA Polymerase I" Biochemistry 15:1510-1516.
Temin and Mizutani, Chapter 7, Entitled "RNA Tumor Virus DNA Polymerases",The Enzymes, Paul Boyer, Academic Press, Inc. London, 1974 ed.
Travaglina and Leob, 1974, "Ribonucleic Acid Dependent Deoxyribonucleic Acid Synthesis by *Escherichia coli* Deoxyribonucleic Acids Polymerase I Characterization of the Polymerization Reaction" Biochemistry 13(15)3010:3017.
Travaglina et al., 1976, "Template Recognition and Chain Elongation in DNA Synthesis in Vitro" J. Mol. Biol. 106:605-621.
Kallen et al., 1962, J. Mol. Biol. 5:248-250.
Karkas, 1973, Proc. Natl. Acad. Sci. USA 70(12):3834-3838.
Loeb et al., 1973, Nature New Biology 242:66-69.
Gulati et al., 1974, Proc. Natl. Acad. Sci. USA 71(4):1035-1039.
Chien et al., 1976, J. Bacteriology 127(3):1550-1557.
Kaledin et al., 1980, Biokhimiya 45(4):644-651.
Ruttimann et al., 1985, Eur. J. Biochem. 149:41-46.
Lawyer et al., 1989, J. Biol. Chem. 264(11):6427-6437.
Tabor and Richardson, 1989, Proc. Natl. Acad. Sci. USA 86:4076-4080.
Kawasaki, "Amplification of RNA Sequences via Complementary DNA (RNA)".
Jones and Foulkes, 1989, Nuc. Acids Res. 17(20):8387-8388.
Shimomaye and Salvato, 1989, Gene Ana. Techn. 6:25-28.
Tse and Forget, 1990, Gene 88:293-296.
Shaffer et al., 1990, Analytical Biochemistry 190:292-296.
Mocharla et al., 1990, Gene 93:271-275.
Levy and Teebor, 1991, Nuc. Acids Res. 19(20):3337-3343.
Lou et al., May, 1991, Clin. Exp. Pharm. Physiology 18:357-362.

*Primary Examiner*—Robert A. Wax
*Assistant Examiner*—Miguel H. Escallon
*Attorney, Agent, or Firm*—George M. Gould; Dennis P. Tramaloni; Stacey R. Sias

[57] ABSTRACT

Methods are provided for the replication and amplification of RNA sequences by thermoactive DNA polymerases. In a preferred embodiment, high temperature reverse transcription is coupled to nucleic acid amplification in a one tube, one enzyme procedure using a thermostable DNA polymerase. Methods for eliminating carry over contamination of amplifications due to prior reverse transcription reactions are also provided.

7 Claims, 4 Drawing Sheets

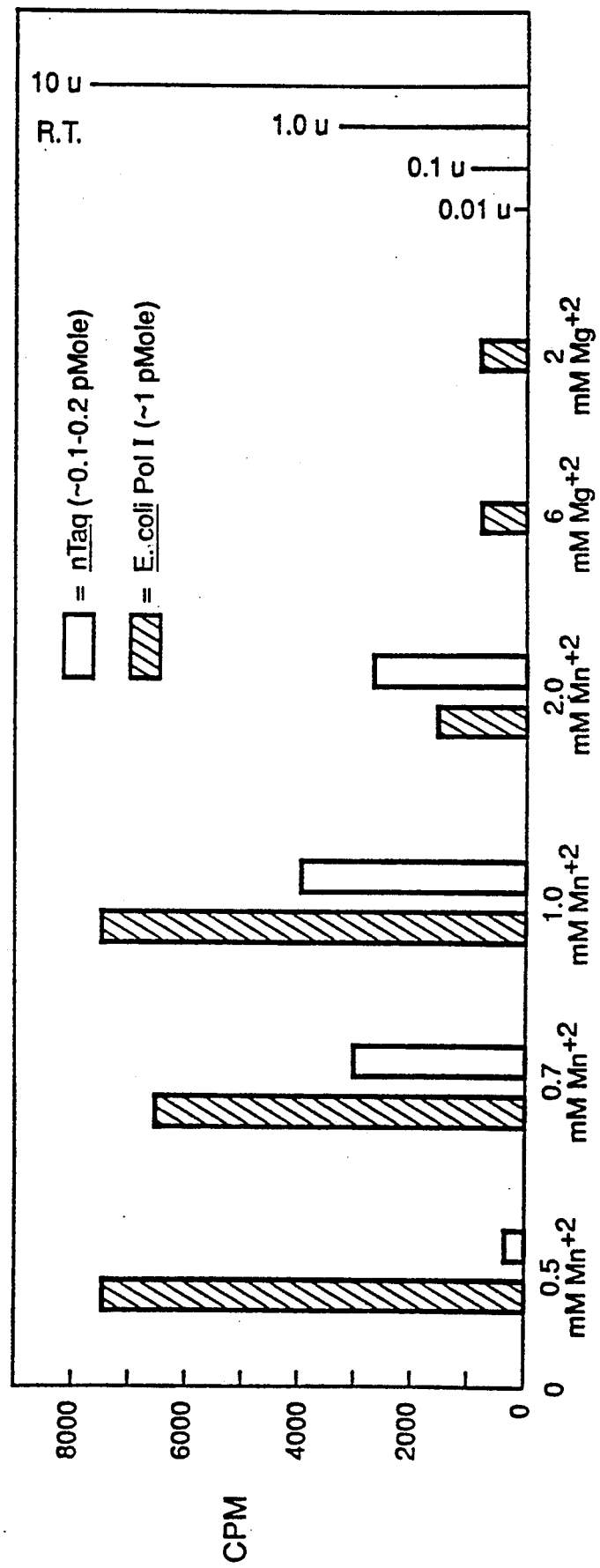
FIG._1

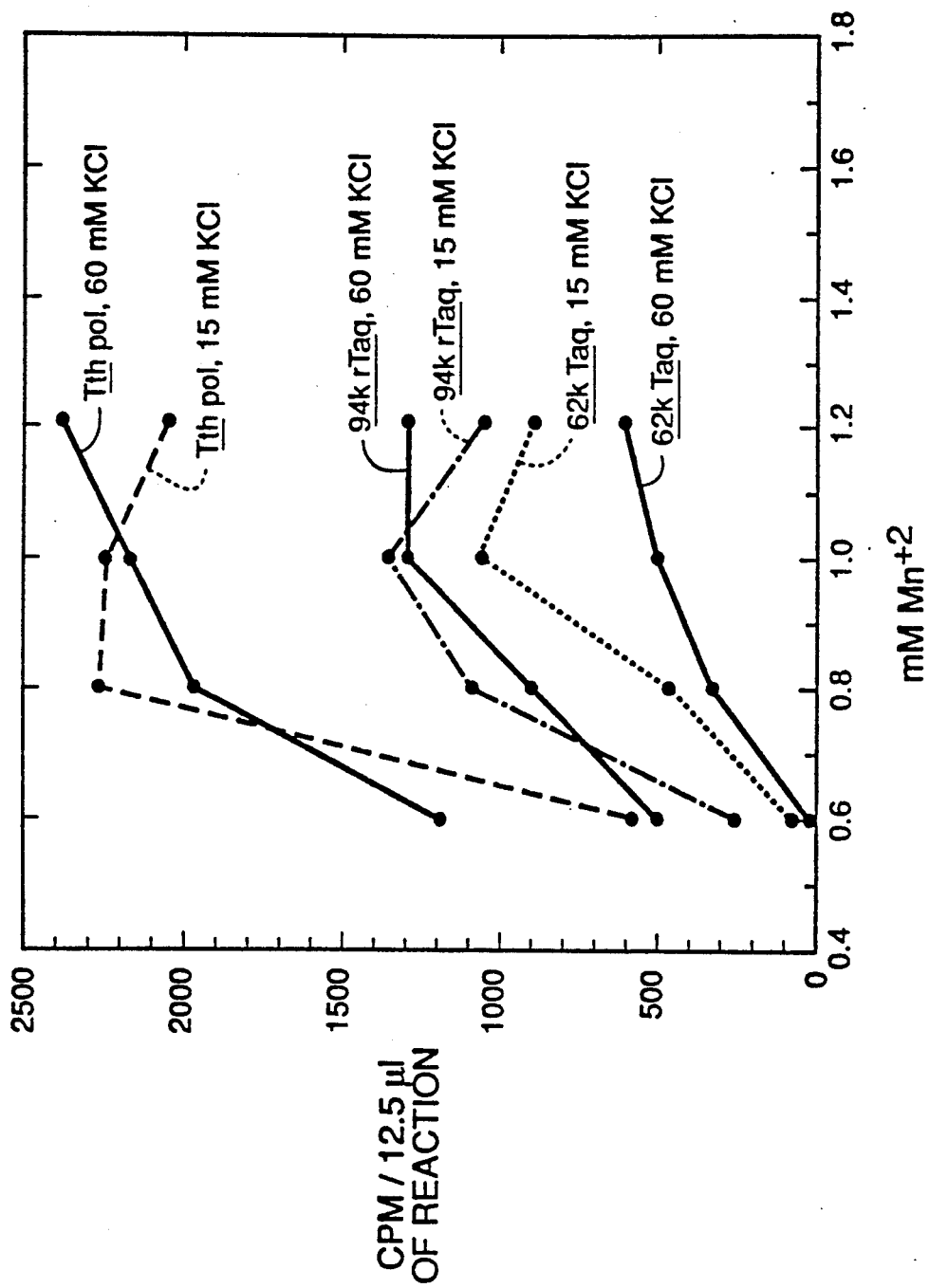
FIG._2

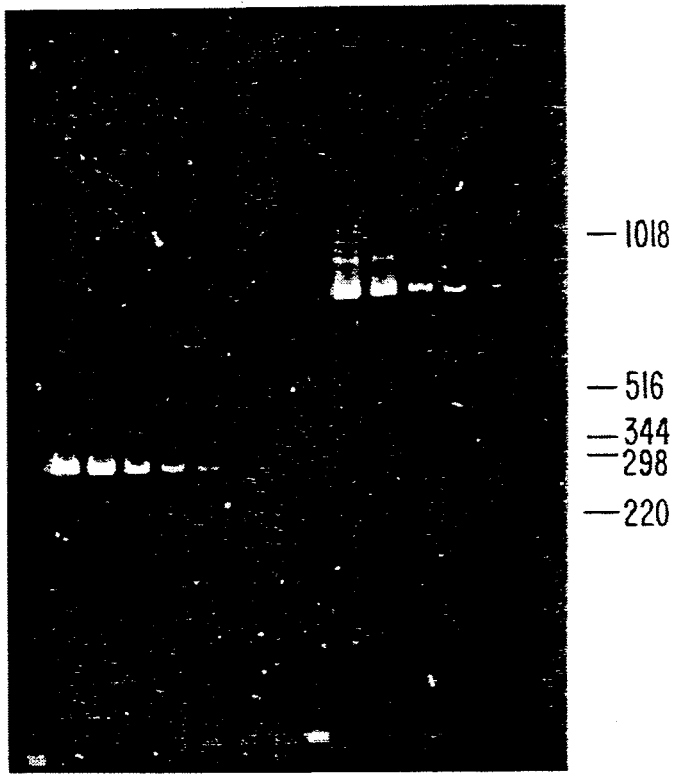
FIG._3

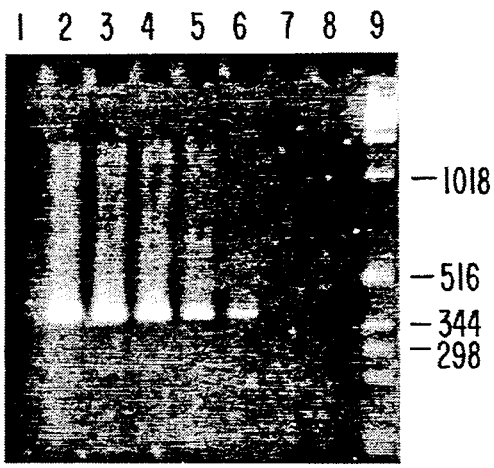
FIG._4
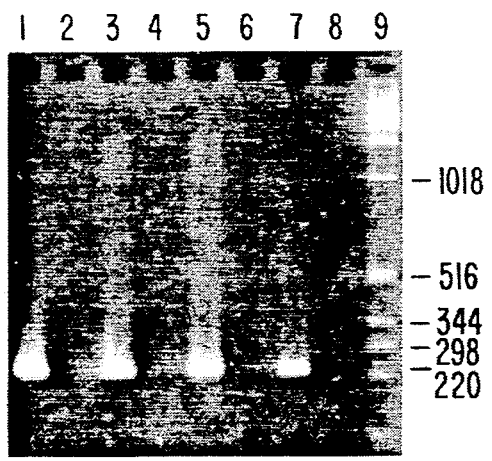
FIG._5

REVERSE TRANSCRIPTION WITH THERMOSTABLE DNA POLYMERASE-HIGH TEMPERATURE REVERSE TRANSCRIPTION

CROSS-REFERENCE

This application is a continuation of application Ser. No. 07/746,121, filed Aug. 15, 1991 now abandoned, which is a continuation-in-part (CIP) of copending PCT/US90/07641, filed, Dec. 21, 1990, which is CIP of Ser. No. 585,471, filed Sep. 20, 1990, now abandoned, which is a CIP of Ser. No. 455,611, filed Dec. 22, 1989. This application is also a CIP of Ser. No. 455,967, filed Dec. 22, 1989, now abandoned which is a CIP of Ser. No. 143,441, filed Jan. 12, 1988, which is a CIP of Ser. No. 063,509, filed Jun. 17, 1987, which issued as U.S. Pat. No. 4,889,818, and which is a CIP of now abandoned Ser. No. 899,241, filed Aug. 22, 1986, now abandoned. This application is also a CIP of Ser. No. 609,157, filed Nov. 2, 1990, now abandoned, which is a CIP of Ser. No. 557,517, filed Jul. 24, 1990, now abandoned.

BACKGROUND OF THE INVENTION

1. Field of the Invention

The present invention relates to the field of molecular biology and provides improved methods for the replication and amplification of ribonucleic acid (RNA) sequences. In a preferred embodiment, the invention provides a method for synthesizing a complementary DNA copy from an RNA template with a thermoactive DNA polymerase. In another aspect, the invention provides methods for coupling reverse transcription of an RNA template and amplification of the resultant DNA using a thermostable DNA polymerase. In a preferred embodiment RNA is reverse transcribed and amplified in a homogeneous, one tube, one enzyme reaction. Methods for sterilization of reverse transcription and reverse transcription/amplification reactions are also provided.

2. Description of Related Art

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Avian myoblastosis virus (AMV) reverse transcriptase was the first widely used RNA-dependent DNA polymerase (Verma, 1977, *Biochem. Biophys. Acta* 473:1).

The enzyme has 5'-3' RNA-directed DNA polymerase activity, 5'-3' DNA-directed DNA polymerase activity, and RNase H activity. RNase H is a processive 5' and 3' ribonuclease specific for the RNA strand of RNA-DNA hybrids (Perbal, 1984, *A Practical Guide to Molecular Cloning*, Wiley & Sons New York). Errors in transcription cannot be corrected by reverse transcriptase because known viral reverse transcriptases lack the 3'→5' exonuclease activity necessary for proofreading (Saunders and Saunders, 1987, *Microbial Genetics Applied to Biotechnology*, Croom Helm, London). A detailed study of the activity of AMV reverse transcriptase and its associated RNase H activity has been presented by Berger et al., 1983, *Biochemistry* 22:2365-2372.

Berger et al. found that the rate limiting step in the reverse transcription of RNA was initiation by the enzyme, rather than the sequential polymerization of additional nucleotides. To overcome this limitation, use of a stoichiometric, rather than catalytic, quantity of reverse transcriptase is frequently recommended (Buell et al., 1978, *J. Biol. Chem.* 253:2471-2482; Wickens et al., 1978 22:2483-2495; Yoo et. al., 1982, *Proc. Nat. Acad. Sci. USA* 80:1194-1198; and Okayama and Berg, 1982, *Mol. Cell. Biol.* 2:161-170). However, when stoichiometric amounts of reverse transcriptase are used, the low level of RNase H activity is significant and may be responsible for fragmented cDNAs and limited cDNA yields (Kotewicz et al., 1988, *Nuc. Acid. Res.* 16:265-277). Christopher et al., 1980, *Eur. J. Biochem.*, 111:4190-4231, and Michelson et al., 1983, *Proc. Nat. Acad. Sci. USA* 80:472-476, have suggested that including an RNase inhibitor in cDNA reactions could alleviate this problem.

DNA polymerases isolated from mesophilic microorganisms such as *E. coli* have been extensively researched (see, for example, Bessman et al., 1957, *J. Biol. Chem.* 233:171-177 and Buttin and Kornberg, 1966, *J. Biol. Chem.* 241:5419-5427). *E. coil* DNA polymerase I (Pol I) is useful for a number of applications including: nick-translation reactions, DNA sequencing, in vitro mutagenesis, second strand cDNA synthesis, polymerase chain reactions (PCR), and blunt end formation for linker ligation (Maniatis et al., 1982, *Molecular Cloning: A Laboratory Manual* Cold Spring Harbor, N.Y.).

Several laboratories have shown that some DNA polymerases are capable of in vitrol reverse transcription of RNA (Karkas, 1973, *Proc. Nat. Acad. Sci. USA* 70:3834-3838; Gulati et al., 1974, *Proc. Nat. Acad. Sci. USA* 71:1035-1039; and Wittig and Wittig, 1978, *Nuc. Acid Res.* 5:1165-1178). Gulati et al. found that *E. coli* Pol I could be used to transcribe Qβ viral RNA using oligo(dT)$_{10}$ as a primer. Wittig and Wittig have shown that *E. coli* Pol I can be used to reverse transcribe tRNA that has been enzymatically elongated with oligo(dA). However, as Gulati et al. demonstrated, the amount of enzyme required and the small size of the cDNA product suggests that the reverse transcriptase activity of *E. coli* Pol I has little practical value.

The use of thermostable enzymes to amplify existing nucleic acid sequences in amounts that are large compared to the amount initially present was described in U.S. Pat. Nos. 4,683,195 and 4,683,202, which describe the polymerase chain reaction (PCR) processes. These patents are incorporated herein by reference. Primers, template, nucleoside triphosphates, the appropriate buffer and reaction conditions, and a polymerase are used in the PCR process, which involves denaturation of target DNA, hybridization of primers, and synthesis of complementary strands. The extension product of each primer becomes a template for the production of the desired nucleic acid sequence. These patents disclose that, if the polymerase employed is a thermostable enzyme, then polymerase need not be added after every denaturation step, because heat will not destroy the polymerase activity.

Thermostable DNA polymerases are not permanently inactivated even when heated to 9320 -95° C. for brief periods of time, as, for example, in the practice of DNA amplification by PCR. In contrast, at this elevated temperature *E. coli* DNA Pol I and previously described reverse transcriptases are inactivated.

The thermostable DNA polymerase from *Thermus aquaticus* (Taq) has been cloned, expressed, and purified from recombinant cells as described in Lawyer et al., 1989, *J. Biol. Chem.* 264:6427-6437, and U.S. Pat. No. 4,889,818 and copending Ser. No. 143,441, filed Jan. 12, 1988, which are incorporated herein by reference. Crude preparations of a DNA polymerase activity isolated from *T. aquaticus* have been described by others (Chien et al., 1976, *J. Bacteriol.* 127:1550-1557, and Kaledin et al., 1980, *Biokymiya* 45:644-651).

The thermostable DNA polymerase from *Thermus thermophilus* (Tth) has also been purified and is described in commonly assigned, copending Ser. No. 455,967, filed Dec. 12, 1989, which is incorporated herein by reference. The '967 patent application also describes that the gene encoding Tth DNA polymerase enzyme from *Thermus thermophilus* has been identified and cloned. Recombinant Tth provides an alternative means preparing the thermostable enzyme. Crude preparations of DNA polymerase activity isolated from *T. thermophilus* have been described by Rüttiman et al., 1985, *Eur. J. Biochem,* 149:41-46. The thermostable DNA polymerase from *Thermotoga maritima* has been identified and cloned and is described in copending Ser. No. 567,244, filed Aug. 13, 1990, now abandoned, and incorporated herein by reference.

PCR requires a nucleic acid template and appropriate primers for amplification. The DNA to be amplified may be synthetic or genomic, contained in a plasmid, or contained in a heterogenous sample. If the nucleotide sequence to be amplified is RNA, the nucleic acid molecule is first treated with reverse transcriptase in the presence of a primer to provide a cDNA template for amplification. Prior to the present invention, amplification of RNA necessitated a reverse transcription step with, e.g., a non-thermostable reverse transcriptase such as Molony Murine Leukemia Virus Reverse Transcriptase (MoMuLV RT) or AMV-RT, followed by treatment of the resulting single-stranded cDNA with a DNA polymerase. The amplification of RNA could be greedy simplified by the availability of a method for reverse transcribing RNA and amplifying DNA with a single enzyme.

Taq polymerase has been reported to inefficiently synthesize cDNA using $Mg^{+2}$ as the divalent metal ion (Jones and Foulkes, 1989, *Nuc. Acids. Res.* 176:8387-8388). Tse and Forget, 1990, *Gene* 88:293-296; and Shaffer et al., 1990, *Anal. Biochem.* 190:292-296, have described methods for amplifying RNA using Taq polymerase and $Mg^{+2}$ ion. However, the methods are inefficient and insensitive. For example, Tse and Forget demonstrate that 4 μg of total RNA is required to generate sufficient PCR product for ethidium bromide-stained gel visualization, using an abundantly expressed mRNA target.

The present invention addresses this need and provides high temperature cDNA synthesis by thermoactive DNA polymerases. The present invention provides improved methods for a one enzyme, one tube, coupled reverse transcription/amplification assay using a thermostable DNA polymerase. The need to open the reaction vessel and adjust reaction components between the two steps is eliminated. The methods offer enhanced sensitivity, simplicity, and specificity over current methods.

SUMMARY OF THE INVENTION

In one aspect, the invention provides a method for amplifying a target RNA molecule in a sample, the method comprising the steps of: (a) treating the sample in a reaction mixture comprising a first and second primer, wherein the first primer is sufficiently complementary to the target RNA to hybridize therewith and initiate synthesis of a cDNA molecule complementary to the target RNA, and the second primer is sufficiently homologous to the target RNA to hybridize to the cDNA and initiate synthesis of an extension product, and a thermostable DNA polymerase in the presence of all four deoxyribonucleoside triphosphates, in an appropriate buffer, wherein the buffer comprises $Mn^{+2}$, at a temperature sufficient for the thermostable DNA polymerase to initiate synthesis of an extension product of the first primer to provide a cDNA molecule complementary to the target RNA; (b) treating the reaction mixture at an appropriate temperature to provide single-stranded cDNA; (c) treating the reaction mixture, at an appropriate temperature for the thermostable DNA polymerase to initiate synthesis of an extension product of the second primer to provide a double-stranded cDNA molecule; and (d) amplifying the double-stranded cDNA molecule of step (c) by a polymerase chain reaction.

The present invention provides methods for sterilizing reverse transcription reactions, amplification reactions, and homogeneous reverse transcription/amplification reactions, contaminated with nucleic acids generated from previous reverse transcription, amplification, and/or homogeneous reverse transcription/amplification reactions. For example the invention provides a method of sterilizing a reverse transcription reaction contaminated with nucleic acids generated from a previous reverse transcription wherein the previous reverse transcription resulted from mixing conventional and unconventional nucleoside triphosphates into a reverse transcription reaction mixture and generating cDNA products having the conventional and unconventional nucleotides incorporated therein, which method comprises degrading the contaminating nucleic acids by hydrolyzing covalent bonds of the unconventional nucleotides.

In another aspect, the invention provides a method of sterilizing a reverse transcription reaction contaminated with nucleic acids generated from a previous homogeneous reverse transcription/amplification reaction wherein the previous homogeneous reaction resulted from mixing conventional and unconventional nucleoside triphosphates into a homogeneous reverse transcription/amplification reaction mixture and generating cDNA and amplified products having the conventional and unconventional nucleotides incorporated therein, which method comprises degrading the contaminating amplified products by hydrolyzing covalent bonds of the unconventional nucleotides.

In one embodiment this method encompasses degrading the contaminating nucleic acid product with uracil-DNA glycosylase in an aqueous solution containing a target nucleic acid sequence; which further comprises inactivating the glycosylase in the presence of the target nucleic acid sequences (such as by heat denaturation); and, reverse transcribing and amplifying the target sequence by a thermostable DNA polymerase. The degradation of the contaminating product may be accomplished while the product is in contact with a nucleic acid reverse transcription/amplification reaction system. Thus, one can prepare a sample for reverse transcription/amplification, treat the sample by the present method to degrade any contaminating nucleic acid generated by a previous reverse transcription, amplification, and/or homogeneous reverse transcription/amplification reaction, and then amplify the target nucleic acid in the sample without having to adjust reaction volume or composition between steps.

BRIEF DESCRIPTION OF THE FIGURES

FIG. 1 is a graph comparing reverse transcriptase activity of *E. coli* Pol I, Taq and MoMuLV reverse transcriptase in MgCl$_2$ and MnCl$_2$ buffers.

FIG. 2 is a graph comparing reverse transcription of an RNA-template, at varying Mn$^{+2}$ concentrations, catalyzed by Tth polymerase, 94 kDa rTaq DNA polymerase, and AmpliTaq™ DNA polymerase, Stoffel Fragment (also referred to as 62 kDa rTaq).

FIG. 3 depicts the results of the coupled RT/PCR assay described in Example V.

FIG. 4 depicts the results of the coupled RT/PCR assay described in Example VI using various amounts of total cellular RNA.

FIG. 5 depicts the results of an RT/PCR assay where different thermostable enzymes are employed for the RT and PCR assays.

DETAILED DESCRIPTION

The present invention provides improved methods for efficiently transcribing and amplifying RNA. These improvements are achieved by the discovery and application of previously unknown properties of thermoactive DNA polymerases. The methods provide a one enzyme procedure for reverse transcribing and amplifying any desired RNA target and replace prior methods requiring more than one enzyme. Methods are provided for a coupled, one tube procedure that eliminates the need to open the reaction vessel for modifying reaction components between the transcription and amplification steps. The invention also provides methods for minimizing the effects of carryover contamination of RNA reverse transcription/amplification assays due to reverse transcribed or amplified products from previous reactions.

The methods comprise treating a sample containing said RNA template with an oligonucleotide primer, which primer is sufficiently complementary to said RNA template to hybridize therewith, and a thermoactive DNA polymerase in the presence of all four deoxyribonucleoside triphosphates, in an appropriate buffer and at a temperature sufficient for said primer to hybridize to said RNA template and said thermoactive DNA polymerase to catalyze the polymerization of said deoxyribonucleoside triphosphates to form a cDNA sequence complementary to the sequence of said RNA template. According to the invention, the DNA polymerase may be thermostable as well as thermoactive.

In another aspect, a primer suitable for annealing to an RNA template may also be suitable for amplification by PCR. For PCR, a second primer, complementary to the reverse transcribed cDNA strand, provides a site for initiation of synthesis of an extension product. As is well known, the thermostable DNA polymerase is able to catalyze this extension reaction on the DNA template; however, until the present invention, no one recognized that the enzyme could also catalyze the RNA-dependent reverse transcription reaction.

In the amplification of an RNA molecule by a thermoactive DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a thermoactive DNA polymerase provides the starting material for amplification.

In another aspect of the invention, a thermostable DNA polymerase can be used in a coupled, one-enzyme reverse transcription/amplification reaction. Methods are provided for both non-homogeneous and homogeneous RT/PCR assays. The term "homogeneous" as used herein refers to a two-step single addition reaction for reverse transcription and amplification of an RNA target. By homogeneous it is meant that following the reverse transcription step, there is no need to open the reaction vessel or otherwise adjust reaction components prior to the amplification step. In a non-homogeneous RT/PCR reaction, following reverse transcription and prior to amplification any one or more of the reaction components is adjusted, added, or diluted including enzyme, primers, divalent cation, salts, pH, or dNTPs.

The term "homogeneous reverse transcription/amplification reaction mixture" refers to an aqueous solution comprising the various reagents used to reverse transcribe and amplify a target RNA. These include enzymes, aqueous buffers, salts, oligonucleotide primers, target nucleic acid, and nucleoside triphosphates. Depending upon the context, the mixture can be either a complete or incomplete homogeneous reverse transcription/amplification reaction mixture.

The present invention provides simplified and improved methods for detecting RNA target molecules in a sample. These methods employ thermostable DNA polymerases to catalyze reverse transcription, second strand cDNA synthesis, and, if desired, amplification. Thus, the invention provides methods which require only one enzyme where previous methods required two. Prior methods also required two sets of incubation conditions, necessitated by the use of different enzymes for each procedure. The methods of the present invention provide RNA transcription and amplification with significantly enhanced specificity and with fewer steps than previous RNA cloning and diagnostic methods. These methods are adaptable for use in kits for laboratory or clinical analysis.

The term "reverse transcription reaction mixture" refers to an aqueous solution comprising the various reagents used to reverse transcribe a target RNA. These include enzymes, aqueous buffers, salts, oligonucleotide primers, target nucleic acid, and nucleoside triphosphates. Depending upon the context, the mixture can be either a complete or incomplete reverse transcription reaction mixture.

For amplification of the cDNA product a number of methods are available to one of ordinary skill in the art. As used herein the term "amplification reaction system" refers to any in vitro means for multiplying the copies of a target sequence of nucleic acid. Such methods include but are not limited to polymerase (PCR), DNA ligase, (LCR), Qβ RNA replicase, and RNA transcription-based (TAS and 3SR) amplification systems.

This invention is not limited to any particular amplification system. As other systems are developed, those systems may benefit by practice of this invention. A recent survey of amplification systems was published in *Bio/Technology* 8:290–293, April 1990, incorporated herein by reference.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture. In the preferred embodiment of the invention the amplification system is PCR and the amplification reaction mixture is a PCR mixture.

The present invention is suitable for transcribing and amplifying RNA from a number of sources. The RNA template may be contained within a nucleic acid preparation from an organism, for example, a viral or bacterial nucleic acid preparation. The preparation may contain cell debris and other components, purified total RNA, or purified mRNA. The RNA template may be a population of heterogeneous RNA molecules in a sample or a specific target RNA molecule.

RNA suitable for use in the present methods may be contained in a biological sample suspected of containing a specific target RNA. The biological sample may be a heterogenous sample in which RNA is a small portion of the sample, as in for example, a blood sample or a biopsied tissue sample. Thus, the method is useful for clinical detection and diagnosis. The RNA target may be indicative of a specific disease or infectious agent.

RNA is prepared by any number of methods; the choice may depend on the source of the sample and availability. Methods for preparing RNA are described in Davis et al., 1986, *Basic Methods in Molecular Biology*, Elsevier, N.Y., Chapter 11; Ausubel et al., 1987, *Current Protocols in Molecular Biology*, Chapter 4, John Wiley and Sons, New York; Kawasaki and Wang, 1989, *PCR Technology*, ed. Erlich, Stockton Press New York; Kawasaki, 1990, *PCR Protocols: A Guide to Methods and Applications*. Innis et al. eds. Academic Press, San Diego; and Wang and Mark, 1990, *PCR Protocols: A Guide to Methods and Applications*, Innis et al. eds. Academic Press, San Diego; all of which are incorporated herein by reference.

In an illustrative embodiment, the RNA template was synthesized in vitro by T7 RNA polymerase transcription from a DNA template. The resulting RNA molecule, referred to as cRNA, may be purified by various means including gel electrophoresis or oligo(dT) chromatography (see Wang et al., 1989, *Proc. Natl. Acad. Sci.* 86:9717, and commonly assigned U.S. Pat. No. 5,219,727, filed Sep. 28, 1989 and issued on Jun. 15, 1993, incorporated herein by reference).

The first step of the present method requires that the RNA template is combined with a suitable primer. As used herein the term "primer" refers to an oligonucleotide capable of acting as a point of initiation of DNA synthesis when annealed to a nucleic acid template under conditions in which synthesis of a primer extension product is initiated, i.e., in the presence of four different nucleoside triphosphates and a thermostable enzyme in an appropriate buffer ("buffer" includes pH, ionic strength, cofactors, etc.) and at a suitable temperature. A suitable primer useful in step (a) of the disclosed methods can hybridize to an RNA template. A primer comprising a sequence sufficiently complementary to a specific RNA target molecule may be used to prime synthesis of the first cDNA strand complementary to a specific target RNA segment if present The primer is sufficiently long to prime the synthesis of extension products in the presence of the thermostable enzyme. The primer may be an oligodeoxyribonucleotide such as oligo(dT).

Oligo(dT) hybridizes to the polyadenylation (polyA) sequence of mRNAs and provides a primer for cDNA synthesis from a heterogeneous population of mRNAs. Because most eukaryotic mRNA molecules contain a polyA sequence at the 3' end, an oligo(dT) primer has general utility in the present methods, for example, in the preparation of a cDNA library.

The primer typically contains 10-35 nucleotides, although that exact number is not critical to the successful application of the method. Short primer molecules generally require lower temperatures to form sufficiently stable hybrid complexes with the template. For oligo(dt) a primer 16-21 nucleotides in length is suitable for high temperature cDNA synthesis according to the disclosed methods; however, it may be preferable to provide an initial incubation at suboptimal temperature to elongate the oligo(dt) primer, thus providing enhanced stability of the primer-template duplex. For example, although Tth pol is only marginally active at temperatures low enough for $d(T)_{16}$ to anneal, the enzyme has sufficient RT activity to extend $d(T)_{16}$ on an RNA template at 42° C. Thus, a preferred method for high temperature reverse transcription using oligo$(dT)_{16-21}$ includes a 5-10 minute room temperature incubation, generally carried out as part of setting up We reaction, followed by 10 minutes at 42° C. and finally 2.5-15 minutes at 70° C. Alternatively, low temperature incubations can be avoided by using oligo(dt) of increased chain length (i.e., oligo$(dT)_{35-45}$). In the present examples of the invention the primers are DNA complementary to a portion of the mRNA molecules encoding the human cytokines interleukin-1-alpha (IL-1$\alpha$) or interleukin-1-beta(IL-1$\beta$). In several examples, the cDNA primer hybridizes to a synthetic RNA template (cRNA).

Synthetic oligonucleotides can be prepared using the triester method of Matteucci et al., 1981, *J. Am. Chem. Soc.* 103:3185-3191. Alternatively automated synthesis may be preferred, for example, on a Biosearch 8700 DNA Synthesizer using cyanoethyl phosphoramidite chemistry.

For primer extension to occur this primer must anneal to the RNA template. Not every nucleotide of the primer must anneal to the template for reverse tranxcription to occur. The primer sequence need not reflect the exact sequence of the template. For example, a non-complementary nucleotide fragment may be attached to the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand.

Prior methods of cDNA preparation required a pre-annealing step. Destabilization of secondary and tertiary structure of the RNA template may be required to allow the primer to hybridize to the RNA. Generally, annealing is accomplished by various means and is routinely accomplished in the presence of an annealing buffer. Maniatis et al. (supra) provide examples of annealing buffers. Annealing methods include, but are not limited to, incubating the RNA/primer mixture at a high temperature for a short period of time followed by step-wise cooling or quick chilling the mixture in a dry ice/ethanol bath. To prevent intra-strand secondary structure interactions from interfering with cDNA synthesis or primer annealing, at the low temperatures used previously for reverse transcription, some investigators modify the RNA template by treatment with chemical denaturants such as methylmercury hydroxide (Baily and Davidson, 1976, *Anal. Biochem.* 70:75). However, such denaturants are generally highly toxic, carcinogenic compounds and must be carefully removed to prevent enzyme inhibition.

According to the present invention, although the primer must anneal to the template for reverse transcription to occur, a separate annealing step is not a necessity. Because thermoactive reverse transcriptase activity is not irreversibly denatured at the high temperatures preferred for stringent annealing, there is no need for the quick chill or step-wise cooling of the denatured template, prior to the addition of the polymerase. Prior methods necessitated that the heated, denatured RNA was cooled in a manner that would maintain the annealed primer-template structure while reducing the temperature to provide conditions compatible with enzyme activity, usually 37°-42° C. The present invention provides methods for high temperature reverse transcription of RNA and eliminates the necessity of a pre-annealing step and the use of chemical denaturants. This aspect of the invention is exemplified in Examples V–XI.

The present methods provide that reverse transcription of the annealed primer-RNA template is catalyzed by a thermoactive or thermostable DNA polymerase. As used herein, the term "thermostable polymerase" refers to an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°-100° C. under polymerization conditions.

In another aspect of the invention, it is only essential that the DNA polymerase for high temperature reverse transcription is thermoactive. As used herein, the term "thermoactive polymerase" refers to an enzyme that is capable of efficiently catalyzing polymerization of deoxyribonucleotides to form a primer extension product complementary to a nucleic acid template strand at temperatures above 60° C. According to the present invention, thermoactive polymerases for reverse transcription have maximal activity over 50° C. The thermoactive DNA polymerase will not irreversibly denature at temperatures between 50° C.-80° C. under conditions for RNA destabilization and primer annealing.

In the examples provided, the thermoactive DNA polymerases are also thermostable; however, a thermoactive, non-thermostable enzyme is also suitable for practicing the present invention. Because the preparation of cDNA from an RNA template does not involve repeated denaturation cycles at elevated temperatures, it is not essential that enzymes useful in the method are thermostable as well as thermoactive. However, in one embodiment of the invention, a homogeneous RT/PCR procedure is provided. Because the reaction components are not adjusted between the RT and PCR steps, a thermostable DNA polymerase is preferred.

The heating conditions will depend on the buffer, salt concentration, and nucleic acids being denatured. Of course, it will be recognized that for the reverse transcription of mRNA, the template molecule is generally single-stranded and, therefore, a high temperature denaturation step is unnecessary. However, double-stranded RNA also provides a suitable template for the reverse transcription/amplification methods described, following an initial denaturation or strand-separation step. Double-stranded RNA templates may include, for example, Reo virus, blue tongue virus, Colorado tick fever virus, and yeast killer factor.

Temperatures for RNA destabilization typically range from 50°-80° C. A first cycle of primer elongation provides a double-stranded template suitable for denaturation and amplification as referred to above. Temperatures for nucleic acid denaturation typically range from about 90° to about 105° C. for a time sufficient for denaturation to occur, which depend on the nucleic acid length, base content, and complementarity between single-strand sequences present in the sample, but typically about 0.5 to 4 minutes.

The thermostable or thermoactive DNA polymerase preferably has optimum activity at a temperature higher than about 40° C., e.g., 60°-80° C. At temperatures much above 42° C., DNA and RNA-dependent polymerases, other than thermostable or thermoactive DNA polymerases, are inactivated. Shimomave and Salvato, 1989, *Gene Anal. Techn.* 6:25-28, describe that at 42° C. AMV-RT has maximum activity. At 50° C. the enzyme has 50% activity, and at 55° C. AMV-RT retains only 10% of its optimal level of activity. Thus, AMV-RT is inappropriate for catalyzing high temperature polymerization reactions utilizing an RNA template. Only the present method provides methods for efficient high temperature reverse transcription with thermoactive DNA polymerases.

Hybridization of primer to template depends on salt concentration as well as composition and length of primer. When using a thermostable or thermoactive polymerase, hybridization can occur at higher temperatures (e.g., 45°-70° C.) which are preferred for increased selectively and/or higher stringency of priming. Higher temperature optimums for the polymerase enzyme enable RNA reverse transcription and subsequent amplification to proceed with greater specificity due to the selectivity of the primer hybridization process. Preferably, the optimum temperature for reverse transcription of RNA ranges from about 55°-75° C., more preferably 65°-70° C.

The present invention provides a method for reverse transcription of an RNA template, having enhanced primer directed specificity, catalyzed by a thermostable DNA polymerase. The methods disclosed are improved over prior methods for the reverse transcription of RNA. These methods provide for the amplification of an RNA segment via an RNA/cDNA hybrid intermediate molecule. The hybrid molecule is a suitable template for amplification by PCR. Thus, the reverse transcription and amplification reactions are coupled. Previous RNA amplification methods require incubation of the RNA/primer mixture in the presence of reverse transcriptase at 37° C.-42° C. prior to the initiation of an amplification reaction. Only by the present invention are all of the enzymatic steps for RNA amplification catalyzed by a thermostable DNA polymerase. The advantages brought to PCR by the commercial availability of Taq and Tth polymerases, the disclosed methods for preparing Tth polymerase, and the commercial availability of Tth DNA polymerase reverse transcription/DNA amplification kits (Perkin Elmer Cetus Instruments) are now, by the methods disclosed herein, applicable to reverse transcription, RNA detection, cDNA preparation and coupled reverse transcription/cDNA amplification of RNA.

DNA amplification procedures by PCR are well known and are described in U.S. Pat. No. 4,683,202. For ease of understanding the advantages provided by the present invention, a summary of PCR is provided. PCR requires two primers that hybridize with the double-stranded target nucleic acid sequence to be amplified. In PCR, this double-stranded target sequence is denatured and one primer is annealed to each strand of the denatured target. The anneal to the target nucleic acid at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990 PCR Protocols: A Guide to Methods and Applications, Academic Press, Inc., San Diego, Calif., which are incorporated herein by reference.

One particular method for minimizing the effects of cross contamination of nucleic acid amplification is described in U.S. Ser. No. 609,157, filed Nov. 2, 1990, now abandoned, which is incorporated herein by reference. The method involves the introduction of unconventional nucleotide bases, such as dUTP, into the amplified product and exposing carryover product to enzymatic and/or physical-chemical treatment to render the product DNA incapable of serving as a template for subsequent amplifications. For example, uracil-DNA glycosylase, also known as uracil-N-glycosylase or UNG, will remove uracil residues from PCR product containing that base. The enzyme treatment results in degradation of the contaminating carryover PCR product and serves to "sterilize" the amplification reaction.

The term "unconventional" when referring to a nucleic acid base, nucleoside, or nucleotide includes modifications, derivations, or analogs of conventional bases, nucleosides or nucleotides which naturally occur in a particular polynucleotide (e.g., DNA [dA, dG, dC, dT] or RNA [A, G, C, U]). Uracil is a conventional base in RNA (i.e., covalent attachment to ribose in a ribopolynucleotide) but an unconventional base in DNA (i.e., covalent attachment to deoxyribose in a deoxyribopolynucleotide). In a coupled RT/PCR reaction, it is desirable to sterilize the reaction prior to the RT step to eliminate carryover nucleic acid products of prior reverse transcription and/or amplification reactions. Sterilization after reverse transcription, and prior to PCR, results in degradation of non-contaminating cDNA products containing dUTP, as well as contaminating product. Synthesis of cDNA in the presence of dTTP and absence of dUTP is impractical. For efficient incorporation of dUTP into the subsequent PCR product, a vast excess of dUTP would be required to dilute the dTTP present as carryover from the reverse transcription step. Furthermore, this would require opening the tube in order to add the dUTP. Consequently, the effectiveness of UNG sterilization would be diminished.

The present invention provides methods for sterilization of the RT/PCR reaction. Example XI demonstrates this aspect of the invention. When unconventional nucleosides are being incorporated into amplification products, routine titration experiments are useful to optimize reaction conditions, and U.S. Ser. No. 609,157, filed Nov. 2, 1990, now abandoned, provides guidance for incorporating unconventional nucleotides. The parameters which are varied include, but are not limited to the concentration of divalent cation, pH range, concentration of polymerase enzyme, concentration of the unconventional nucleoside, the addition of natural nucleoside for which the unconventional nucleoside is inserted, time of each cycle, and temperature.

Generally, the concentration of dNTPs in a PCR is within the range 20-200 $\mu$M each dNTP. For incorporating dUTP the efficiency of amplification is improved at an elevated nucleotide concentration. In Example XI, the concentration of dNTP in the PCR is 200 $\mu$M and dCTP, dGTP, and dATP are also present at the same concentration, although this is not essential. The concentration Of $MgCl_2$ is increased accordingly, on an equimolar basis, when the concentration of dNTP is increased. In Example XI, the PCR contains 200 $\mu$M of each dGTP, dATP, dUTP, and dCTP and 2 mM $MgCl_2$, and provides efficient amplification.

For reverse transcription using a thermostable polymerase, $Mn^{+2}$ is preferred as the divalent cation. $Mn^{+2}$ is included as a salt, for example, $MnCl_2$. The $MnCl_2$ is generally present at a concentration of 0.5-7.0 mM, and 0.8-1.4 mM is preferred when 200 $\mu$M of each dGTP, dATP, dUTP, and, dCTP are utilized; however, 1.2 mM $MnCl_2$ is most preferred. As noted above for amplification, the optimal concentration of the unconventional nucleotide, and divalent cation may vary in the reverse transcription reaction, depending on the total dNTP concentration and on the particular primers, template, and polymerase present.

In one embodiment of the invention, at Example X, a two-step single addition procedure is provided for coupled RT/PCR. In the method, following reverse transcription, there is no buffer adjustment required prior to PCR. Manganese serves as the divalent cation for both the RT and PCR steps. For incorporating either dTTP or dUTP, using 200 mM dNTPs, the concentration of $MnCl_2$ is lowered to avoid a reduction in amplification efficiency that may occur when MnCl$_2$ concentration is maintained at 1.2 mM during PCR.

Following amplification and analysis of the RT/PCR result, the RT/PCR product may be introduced unintentionally as a contaminant in other reactions. Prior to subsequent RT, RT/PCR or amplification reactions, the reaction mixtures ar-e treated with a DNA glycosylase specific for the unconventional nucleotide incorporated during the prior RT/PCR. In this manner, any previous RT/PCR product, present as a contaminant in subsequent RT, RT/PCR or amplification reaction mix containing a target nucleic acid, is hydrolyzed.

Consequently, in practice, the sterilization treatment is carried out prior to the RT/PCR assay to eliminate carryover of dUTP containing product DNAs. For example, prior to the 70° C. incubation of the reverse transcription mix, 0.2–1.0 units UNG per 20 μl RT/reaction is added and incubated for 1–10 minutes at room; temperature. The subsequent 70° C. RT and 95° C. denaturation steps serve to inactivate UNG so that newly synthesized cDNA and PCR products are not degraded. UNG is commercially available from Perkin Elmer Cetus Instruments. U.S. Ser. No. 609,157 describes methods for producing UNG by recombinant means and also themiolabile UNG derivates which do not regain activity after heating above the denaturation temperature of the DNA sample. Such derivates may be preferred for practicing the present invention.

The target of amplification can be an RNA/DNA hybrid molecule. The target can be a single-stranded or double-stranded nucleic acid. Although the PCR procedure described above assumed a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the motion mixture contains a double-stranded cDNA molecule. At this point, successive cycles of amplification proceed as described above. In the present methods, the target of amplification is a single-stranded RNA, and the first amplification cycle is the reverse transcription step. Alternatively, if the starting template is double-stranded RNA, an initial high temperature denaturing step may be used to prepare single-stranded RNA template.

As used herein the term "cDNA" refers to a complementary DNA molecule synthesized using a ribonucleic acid strand (RNA) as a template. The RNA may be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

The methods of the present invention provide means for obtaining cDNA from a desired RNA template wherein the desired end product is produced with greater specificity than by previous methods. Additionally, the present invention provides that cDNA synthesis can be coupled to amplification by PCR. These methods incorporate previously unknown properties of thermoactive DNA polymerases. In the disclosed embodiments, methods are provided which utilize Taq and Tth polymerases for reverse transcription. These embodiments should not be construed as a limitation of the present invention.

Thermostable polymerases are available from a number of sources. The enzyme may be a native or recombinant protein. A preferred thermostable enzyme is *Thermus thermophilus* DNA polymerase Tth polymerase), purified from *Thermus thermophilus* (see copending Ser. No. 455,967, now abandoned in favor of continuation application Ser. No. 07/880,478, filed May 6, 1992, and also published as WO91/09950, which is incorporated herein by reference). Alternatively, Tth is purified from recombinant host cells as described herein and may be designated as rTth. Also preferred for practicing the invention is Taq polymerase. Taq is commercially available as a recombinant product or purified as native Taq from *Thermus aquaticus* (Perkin Elmer-Cetus Inst.). As used herein, recombinant Taq may be designated as rTaq and native Taq may be designated as nTaq.

An important aspect of the present invention relates to Tth DNA polymerase for reverse transcription and amplification of nucleic acids. Tth polymerase is commercially available from Perkin Elmer Cetus Instruments. The gene encoding this enzyme has been cloned from *T. thermophilus* genomic DNA. Tth polymerase has a predicted molecular weight of about 94 kDa, based on the inferred amino acid sequence. The complete coding sequence (~2.5 kb) for the Tth polymerase can be easily obtained in an ~3.7 kilobase (kb) HindIII-BstEII restriction fragment of plasmid pBSM: Tth, although this ~3.7 kb fragment contains an internal HindIII restriction enzyme site. One specific isolate of pBSM:Tth in *E. coli* K12 strain DG101 was purified and referred to as pBSM:Tth10. This plasmid was deposited with the American Type Culture Collection (ATCC) in host cell *E. coli* K12 strain DG101 on Dec. 21, 1989, under ATCC accession No. 68195. The availability of the Tth DNA polymerase gene sequence provides the necessary starting material for one skilled in the art to prepare any number of expression vectors applicable to a variety of host systems for preparing recombinant Tth DNA polymerase. Similarly, mutant forms of the polymerase may be prepared that retain the DNA polymerase activity and are within the meaning of the term *Thermus thermophilus* DNA polymerase.

A number of Tth DNA polymerase expression vectors are described in copending Ser. No. 455,967, which are suitable for producing recombinant purified Tth for use in the present invention, and that application is incorporated herein by reference. Of these expression vectors, plasmid pLSG33 *E. coli* K12strain DG116 was used as a source of recombinant Tth. In plasmid pLSG33, expression of the gene encoding Tth polymerase is regulated by the $\lambda P_L$ promoter. Construction of pLSG33 described in detail in co-pending Ser. No. 455,967, now abandoned in favor of continuation application Ser. No. 07/880,478, filed May 6, 1992, and also published by WO91/09950 and incorporated herein by reference. In that description pBSM:Tth is utilized as the source of the Tth gene.

Once the Tth DNA polymerase has been expressed in a recombinant host cell, the enzyme can be purified and used in the methods disclosed herein. Purification procedures have been previously described for native Tth and native and recombinant Taq in Ser. No. 455,611 filed Dec. 22, 1989, and Ser. No. 143,44 1, filed Jan. 12, 1988, now abandoned, and the disclosure of which are incorporated herein by reference. Purification of recombinant Tth polymerase is generally similar, and the previously described processes are suitable. However, a preferred method for purifying recombinant Tth is provided in Example I in the present specification. The procedure for purifying recombinant Tth is simplified over the native Tth purification scheme. Because the non-native host cell does not produce TthHB8 endonuclease I, which co-elutes with native Tth polymerase, the steps taken to remove TthHB8I endonuclease are not needed.

Although the present invention is exemplified by Taq and Tth DNA polymerases, the invention is not limited to that description. Other thermostable polymerases that have been reported in the literature win also find use in the practice of the methods described. Examples of these include polymerases extracted from the thermophilic bacteria *Bacillus stearothermophilus, Thermosipho africanus, Thermotoga maritima,* Thermus species SPS17, *T. flavus, T. lacteus, T. rubens, T. ruber,* and T. species, Z05. In addition, thermostable polymerases isolated from the thermophilic archaebacteria include, for example, *Desulfurococcus mobilis, Methanobacterium thermoautotrophicum, Methanothermus fervidus, Pyrococcus furious, Pyrodictium occultum, Sulfolobus acidocaldarius, S. solfataricus, Thermococcus litoralis,* and *Thermoplasma acidophilum.*

Modified thermostable polymerases may result from proteolytic degradation or may be produced from a truncated gene. These proteins are also useful in the practice of the present invention so long as they function to polymerize deoxyribonucleoside triphosphates using an RNA template.

Taq polymerase can be prepared as both a 94 kDa and 61 kDa enzyme. The 61 kDa been previously referred to as the 62 kDa enzyme (see for example U.S. Pat. No. 4,889,818) and may be referred to as the Stoffel Fragment; however, the Taq 61 kDa, 62 kDa, and Stoffel Fragment enzyme all refer to the same identity. The Stoffel Fragment is a processed form of the 94 kDa enzyme, resulting from proteolytic cleavage of the N-terminal region. Alternatively, the Stoffel fragment enzyme can be made directly as a recombinant protein. The Stoffel Fragment is composed of approximately two-thirds of the carboxy-terminal portion of the full length protein. Either form of the enzyme will function to reverse transcribe RNA as described herein. In addition to the N-terminal deletion, individual amino acid residues may be modified by oxidation, reduction, or other derivatization, or the protein may be cleaved to obtain fragments that retain activity.

Thus, modification to the primary structure itself by deletion, addition, or alteration of the amino acids incorporated into the sequence during translation can be made without destroying the high temperature DNA polymerase activity of the protein. Such substitutions or other alterations result in proteins useful in the methods of the present invention. The availability of DNA encoding these sequences provides the opportunity to modify the codon sequence to generate mutant protein forms also having reverse transcriptase activity.

As demonstrated herein, Lb DNA polymerase has high reverse transcriptase activity. However, Tth polymerase, as well as Taq polymerase, lacks a 3' to 5' exonucleolytic proofreading activity. This 3' to 5' exonuclease activity is generally considered to be desirable because it allows removal of misincorporated or unmatched bases in the newly synthesized nucleic acid sequences. Because the lack of a proofreading activity may effect enzyme fidelity, the presence of a proofreading exonuclease would be a novel and potentially useful property for a reverse transcriptase.

*Thermotoga maritima* DNA polymerase (Tma pol) has 3' to 5' exonuclease activity. U.S. patent application Ser. No. 567,244, filed Aug. 13, 1990, and incorporated herein by reference, provides means for isolating and producing Tma polymerase. That patent application provides the amino acid and nucleic acid sequences for Tma DNA polymerase and describes the amino acid domains for various enzyme activities, including the 3' to 5' exonuclease activity, as well as the 5' to 3' exonuclease activity.

Accordingly, domain shuffling or construction of chimeric DNA polymerases may be used to provide thermostable DNA polymerases containing novel properties. For example, a thermostable chimeric DNA polymerase which has the 3' to 5' exonuclease domain of Tma polymerase incorporated into Tth polymerase can be constructed using "overlap" PCR (Higuchi, 1989, *PCR Technology supra.*). In this method, the intended junction sequence is designed into the PCR primers (at their 5' ends). Following the initial amplification of each individual domain, the various products are diluted (ca. 100- to 1,000-fold) and combined, denatured, annealed, extended, and then the final forward and reverse primers are added for an otherwise standard PCR.

Specifically, the polymerase domain of Tth polymerase (amino acids 415–834) is joined to the 5' to 3' and 3' to 5' exonuclease domains of Tma polymerase (amino acids 1–475). For example, a Tth polymerase expression vector and a portion of the gene encoding Tma polymerase can be combined as follows. The expression vector pLSG33 is described in copending Ser. No. 455,967 now abandoned in favor of continuation application Ser. No. 07/880,478, filed May 6, 1992, and published as WO91/09950 and contains the gene encoding Tth. Plasmid pTMA5'Nd#3 (subsequently referred to as pTma06), described in copending Ser. No. 567,244, filed Aug. 13, 1990, now abandoned, which is incorporated herein by reference, contains the 5' portion of the gene encoding polymerase. To prepare the plasmid for overlap PCR, the pLSG33 and pTma06 are linearized with NdeI and used in two separate PCR amplifications using primers A and B for the Tma polymerase, and primers C and D for the Tth polymerase. The primers' sequences are:

| A | SEQ ID NO: 1 | 5'-GGCATATGGCTAGACTATTTCTTTTTG-3' |
|---|---|---|
| B | SEQ ID NO: 2 | 5'-AGGTTCCGATGAAGTCTGTAGGTGATGTCTG-3' |
| C | SEQ ID NO: 3 | 5'-CTACAGACTTCATCGGAACCTCCTTAAGCG-3' |
| D | SEQ ID NO: 4 | 5'-CCAACCCGCCTCGGCCACGAAGG-3' |

In addition to the region of complementation designed into primers B and C, primer A has an Nde I site incorporated into its 5'-termini. Primer D corresponds to a portion of the polymerase domain of Tth and is directly distal to a BamHI site within the 3' region of the Tth gene. The first round of PCR generates product AB (1441 bp) and product CD (586 bp). Following the initial amplification of the individual domains, the reactions are diluted approximately 100- to 1000-fold and combined, denatured, annealed, and extended using the final forward and reverse primers (primers A and D, respectively). The final product, AD, is digested with Nde I and BamHI to provide a 2006 bp product. This product is then ligated back into the expression vector (following digestion of the vector, pLSG33, with Nde I and BamHI) and transformed into an appropriate host. The chimeric protein wig contain 895 amino acid residues.

Tth, Taq, and Tma DNA polymerases also contain a 5' to 3' exonuclease activity which may be responsible for RNase H activity. The elimination or reduction of 5' to 3' exonuclease activity by, for example, site specific mutagenesis, may provide a preferred form of thermostable DNA polymerase for cDNA synthesis. A substitution of glutamic acid for a glycine residue at amino acid number 103 of the pol A gene of *E. coli* has been demonstrated to produce a polypeptide defective in 5' to 3' exonuclease activity (Kingsbury and Helinski, 1973, *J. Bacteriol.* 114:1116–1124; Olivera and Bonhoeffer, 1974, *Nature* 250:513–514; and Joyce et al., 1985, *J. Mol. Biol.* 186:283–293). The homologous amino acid is conserved in Tth polymerase (amino acid number, 108). The normal GGG codon is mutated to a GAA codon by PCR to provide a novel thermostable DNA polymerases with improved characteristics for reverse transcription of RNA. Alternatively, changing Tth amino acid number 46 from glycine to aspartic acid may also effect the 5'→3'exonuclease activity providing a novel enzyme.

The fidelity of viral reverse transcriptases, such as AMV-RT and MoMuLV-RT, is compared to thermoactive reverse transcriptases by a straightforward assay procedure. Plasmid BS+ (Stratagene) is used for such an assay. The plasmid encodes an α-complementing β-galactosidase activity and can be linearized with Nde I. T3 RNA polymerase is used to prepare a cRNA transcript of the α donor region. After treatment of the cRNA with RNase-free DNase and isolation of the cRNA, the cRNA is used as a template for a reverse transcription/amplification reaction. A reverse transcription primer complementary to the 3' end of the cDNA containing an Nde I sequence at its 5' terminus, and an upstream PCR primer comprising a Pst I sequence at the 5' termini provide a 752 bp PCR product. The PCR product and the pBS+ vector are then digested with Nde I and Pst I followed by ligation of the PCR product into the vector and transformation into a suitable host The presence of white colonies indicates that a mutation had occurred during the RT or PCR amplification. The assay provides means for assigning a relative value to the fidelity of the reverse transcriptase activity of various enzymes. Specific mutations can be determined by sequence analysis.

The method of high temperature reverse transcription provides novel means for the detection of specific RNAs in a sample. This method is useful in a clinical setting to monitor, for example, retrovirus infection in children born to AIDS victims or to monitor the expression of diagnostic proteins. Detection of the reverse transcribed or amplified products can be accomplished by any of a number of known means. Such means include, but are not limited to, hybridization with isotopic or non-isotopically labeled probes in, for example, a dot blot or electrophoretic format. A detection format may include a capture step, such as a solid support substrate and avidin-biotin label system. U.S. Pat. No. 5,210,015, filed Aug. 6, 1990 and issued on May 11, 1993, incorporated herein by reference, describes a method for use of the 5' to 3' nuclease activity of a nucleic acid polymerase. According to the method, a labeled nucleic acid probe in a hybridized duplex composed of a labeled oligonucleotide and a target oligonucleotide is degraded. Labeled fragments are subsequently detected. Detection may also include quantitative analysis to monitor progress of, for example, an infection or response to a treatment regimen. Alternatively, detection may be for the purpose of cell typing.

Primers can be designed with convenient restriction enzyme recognition sequences located at or near the 5' end of the primer. In the formation of the cDNA transcript, so long as the 3' end of the primer is hydrogen-bonded to the target sequence, the resulting double-stranded cDNA molecule would contain a specific restriction enzyme recognition sequence. Following amplification, using the cDNA as a template, the restriction site could be used to facilitate other procedures, for example, cloning.

Following reverse transcription of RNA by a thermoactive or thermostable DNA polymerase, the RNA can be removed from the RNA/cDNA hybrid by heat denaturation or by a number of other known means such as alkali, heat, or enzyme treatment. Enzyme treatment may consist of, for example, treating the RNA/cDNA hybrid with RNase H. RNase H is specific for RNA strands within an RNA/DNA double-stranded molecule. Tth and Taq associated RNase H and 5'→3' nuclease activities can facilitate hydrolysis of the RNA template and synthesis of the second DNA strand, as well as primer extension for amplification of the cDNA sequence. Alternatively, exogenous RNase H is added from a commercially available source.

The RNase H activity of thermostable polymerases provides means for distinguishing between RNA and DNA templates in a sample. This is particularly useful for detecting RNA in the presence of homologous duplex DNA. Where the DNA is free of introns in, for example, proviral HIV DNA in sera or plasma, amplified RNA and DNA may not be distinguishable by size. However, following reverse transcription, thermostable RNase H activity eliminates the necessity for denaturing the RNA/cDNA duplex. Consequently, in the presence of genomic or proviral DNA, only the RNA template is amplified in the first PCR cycle.

In a preferred method for distinguishing between homologous RNA and DNA templates, amplification primers are used that will effectively lower the denaturation temperature of the PCR product. For example, for detecting HIV RNA, primer pairs SK462 SEQ ID NO: 5 (5'AGTTGGAGGACATCAAGCAGCCATG-CAAAT)/SK431 SEQ [D NO: 6 (5'TGCTATGT-CAGTTCCCCTTGGTTCTCT) and SK38 SEQ ID NO: 7 (5'ATAATCCACCTATCCCAGTAG-GAGAAAT)/SK39 SEQ ID NO: 8 (5'TTTGGTCCTTGTCTTATGTCCAGAATGC) generate a PCR product that is denatured well below 94° C. Typical denaturation temperatures for PCR are 94°–96° C. At the lowered temperature the double-stranded DNA (i.e. the expected "contaminant") is not denatured and would not be amplified. Methods for affecting the denaturation temperature of PCR products are described in detail in copending U.S. Ser. No. 718,576, filed Jun. 20, 1991, now abandoned in favor of U.S. Ser. No. 08/033,072, filed Mar. 10, 1993, now allowed, and incorporated herein by reference.

Alternatively, unconventional nucleotides are useful for effecting the denaturation temperature of the PCR product. For example, hydroxymethyl dUTP (HmdUTP) naturally occurs in SP01 phage DNA as 5' hydroxymethyluracil (HmUra) in place of thymine (Kallen et al., 1962, *J. Mol. Biol.* 5:248-250, and Levy and Teebor, 1991, *Nuc. Acids Res.* 19(12):3337). The HmUra containing genome melts at 10° C. less than DNA of corresponding thymine content. Incorporation of HmdUTP into cDNA effectively lowers the denaturation temperature of the reverse transcribed product, in comparison to the denaturation temperature of the homologous DNA. Other modified nucleoside triphosphates capable of effecting the Tm of the DNA product (e.g., C7dGTP, 7, 7 deaza-2'deoxy guanosine triphosphate) are also suitable for distinguishing between homologous RNA and DNA templates.

Following removal or melting of the RNA template strand, the remaining cDNA strand can then serve as a template for polymerization of a self-complementary strand, providing a double-stranded cDNA molecule suitable for additional amplification, detection or other manipulation. The second strand synthesis also requires a primer. A sequence specific primer can be introduced into the reaction mix to prime second strand synthesis. Alternatively, a duplex adapter-linker may be ligated to the cDNA or the cDNA may be tailed with a terminal transferase-type activity. The second strand primer needs only to hybridize to the tail rather than the specific cDNA sequence (see for example, Frohman in Innis et al. supra.). In the practice of the disclosed methods, it may be desirable to use a fu-st set of primers to synthesize a specific cDNA molecule and a second nested set of primers to amplify a desired cDNA segment. AU of these reactions may be catalyzed by the same thermostable DNA polymerase.

DNA polymerases require a divalent cation for catalytic activity. Tabor and Richardson, 1989, *Proc. Natl. Acad. Sci.* USA 86:4076-4080, have reported that Mn2+ can be substituted for Mg$^{2+}$ in DNA sequencing methods. These methods require a DNA template and T7 DNA polymerase or *E. coli* DNA polymerase I.

Either Mn$^{+2}$, Mg$^{+2}$, or Co$^{+2}$ can activate Taq, Tth, and Tma DNA polymerases; however, Mn$^{+2}$ is preferred in the present method. In the disclosed embodiments of the invention, buffers are provided which contain Mn$^{+2}$ for nucleic acid reverse transcription from an RNA template. These buffers are improved over previous reverse transcription buffers and result in increased cDNA yields. In particular, practice of the present methods using Tth and MnCl$_2$ for amplifying RNA imparts an increase in sensitivity of at least 10$^6$ fold compared to MgCl$_2$ and standard PCR conditions.

For reverse transcription, according to the present invention, the primer-template mixture is incubated with a thermoactive or thermostable polymerase under suitable polymerization conditions. These conditions are provided by a buffer containing a divalent cation, a monovalent cation, all four deoxyribonucleotide triphosphates (dNTPs), and a buffering agent. In the present embodiments, for reverse transcription the divalent cation supplied is MgCl$_2$, MgOAc, or MnCl$_2$ in a concentration ranging from 0.5 mM to 7 mM for MnCl$_2$ or 0.5 to 10 mM MgCl$_2$. Preferably, the divalent cation is MnCl$_2$ at a concentration between 0.5 and 2 mM.

The monovalent cation may be supplied by KOAc, NaCl, or KCl. For KCl the concentration is between 1-200 mM, preferably the concentration is between 40 and 100 mM, although the op&hum concentration may vary depending on the polymerase used in the reaction. Optimal reverse transcriptase activity is observed between 50 and 75 mM KCl when Tth polymerase is used. However, enhanced RT/PCR is observed when the KCl concentration is increased up to 100 mM. For AmpliTaq ® DNA polymerase, 50 mM KCl is preferred. Deoxyribonucleotide triphosphates are added as solution of the salts of dATP, dCTP, dGTP, dUTP, and dTTP, such as disodium or lithium salts. In the present methods a final concentration in the range of 1 µM to 2 mM each is suitable, and 100-600 µM is preferred. Although the optimal concentration of the nucleotides may vary in the reverse transcription reaction, depending on the total dNTP concentration and on the particular primers and template. For longer products, i.e., greater than 1500 bp, 500 µM each dNTP and 2 mM MnCl$_2$ may be preferred.

In one embodiment of the invention, a method for homogeneous RT/PCR is provided. This two-step, single addition procedure eliminates the need to open the tube after the addition of initial reagents. Thus, the opportunity for contamination between the RT and PCR steps is removed. Due to the high enzyme concentration required for optimum RT activity, a short extension cycle is preferred, i.e., 10-30 seconds, during each PCR thermocycle. Because there is no buffer adjustment between the RT and PCR steps, in a homogeneous RT/PCR assay MnCl$_2$ is preferably less than 1.0 mM and, most preferably, 0.8 mM. However, the addition of a metal buffer such as isocitrate allows higher MnCl$_2$ to be used. Although in the presence of dUTP, the RT step is more efficient at the high MnCl$_2$ concentration, the PCR step is less efficient Most preferably 0.8 mM MnCl$_2$ is Used and the product is detected by means more sensitive that ethidium stained gels; i.e., probe hybridization or incorporation of labeled, or other detectable nucleotides.

A suitable buffering agent is Tris-HCl, pH 8.3, although the pH may be in the range 8.0-8.8. The Tris-HCl concentration is from 5-50 mM, although 10-20 mM is most preferred. Additionally, EDTA less than 0.5 may be present in the reverse transcription reaction mix. Detergents such as Tween-20 TM and Nonidet TM P-40 are present in the enzyme dilution buffers. A final concentration of non-ionic detergent approximately 0.1% or less is appropriate, however, 0.05%-0.01% is preferred and will not interfere with polymerase activity. Similarly, glycerol is often present in enzyme preparations and is generally diluted to a concentration of 1-10% in the reaction mix. A mineral oil overlay may be added to prevent evaporation.

The present methods require only that RNA is present in the sample. In an example, a synthetic RNA prepared using a plasmid containing a T7 promoter is reverse transcribed and amplified by the methods of the present invention. In another example, a heterogeneous population of total cellular RNA is used to reverse transcribe and amplify a specific mRNA. For practicing the invention the amount of RNA present in the sample is generally within the range of 0.1 pg to 1 µg. The amount required and the results will vary depending on the complexity of the sample RNA and the type of detection utilized. Because of the specify of the high temperature reverse transcription reaction, 10 to 10$^8$ molecules of the target RNA are sufficient to provide up to or exceeding microgram quantities of PCR product. In several of the disclosed examples, amplification products are visualized by ethidium bromide staining after gel electrophoresis of 5% of the total reaction mix. Thus, the amount of target required would be substantially reduced when alternative means for assay of the product is utilized. For example, isotopically labeled DNA probes suitable for detecting the electrophoresed PCR products would increase the sensitivity of detection and therefore decrease the amount of starting material required (e.g., 1–10$^8$ molecules of target RNA in the sample).

Preferably, the amount of RNA present in the reverse transcription reaction is 10 pg to 500 ng and most preferably 0.1 to 300 ng. In this preferred range, 1 to 10 units of thermoactive DNA polymerase is sufficient for providing a full length cDNA product. To achieve predominantly full length cDNA, the enzyme to template ratio is preferably greater than 0.5. When the sample contains more than 300 ng of RNA, it may be desirable to include additional enzyme to ensure transcription of a full length cDNA product from the RNA template. However, if the reverse transcription reaction is coupled to PCR, the effect of high enzyme concentration in the PCR reaction should be considered. For example when Taq is used as the thermoactive polymerase, high enzyme concentrations can result in non-specific PCR products and reduced yields (see Saiki in *PCR Technology* Ed. Erlich, 1989, Stockton Press). The potential problems resulting from a high enzyme concentration, however, are easily avoided by inactivating the thermoactive DNA polymerase between the reverse transcription reaction and the amplification reaction. Inactivation is achieved by incubating the cDNA synthesis reaction mix at 99° C. for 3 to 10 minutes. An appropriate amount of thermostable DNA polymerase is then added back to the reaction mix, and PCR is conducted as usual. This method is also suitable when different thermostable DNA polymerases are used for each of the two reactions, as exemplified in Example VII.

Once the sample containing RNA has been prepared and the suitable primer and salts have been added, the reaction is incubated with the thermoactive DNA polymerase for 1–60 minutes. Usually, however, a reaction time of 2 to 30 minutes is suitable. For a target molecule that is relatively short (~300 nucleotides), the reverse transcription reaction is preferably incubated for approximately 2–5 minutes. If the target molecule is long, or if the ratio of total RNA to target RNA is high, e.g., 100 copies of target RNA in the presence of 250 ng of total RNA, an incubation time of 10–30 minutes is preferred.

It is preferred, but not essential that the thermoactive DNA polymerase is added to the reverse transcription reaction mix after both the primer and the RNA template are added. Alternatively, for example, the enzyme and primer are added last, or the MnCl$_2$, or template plus MnCl$_2$ are added last It is generally desirable that at least one component, that is essential for polymerization not be present, until such time as the primer and template are both present and the enzyme can bind to and extend the desired primer/template substrate application Ser. No. 481,501, filed Feb. 16, 1990, now abandoned, which is incorporated herein by reference).

In practicing present methods the reaction mix is incubated above 40° C., although a preferred temperature is 55°–75° C. At this temperature, the specificity of the primer-template annealing is enhanced over the annealing specificity at a lower temperature, and the thermoactive enzyme has higher activity at the elevated temperature. The elevated temperature reduces non-specific priming by degraded native nucleic acid and by incorrect primer-template hybridization.

Following reverse transcription, the RNA template may be degraded or alternatively denatured, providing a template for continuous replication resulting in an excess of single-stranded DNA molecules. This excess of single-stranded DNA can be detected by standard probe hybridization techniques. Thus, the invention provides means for direct detection of target segments. The resulting nucleic acid products can be detected by a number of electrophoretic or chromatographic means. The use of a radiolabeled triphosphate is helpful in monitoring the extent of the reaction and the size of products formed, although this is not an essential component of the invention.

The reverse transcription reaction products are suitable as templates for amplification by PCR. In one embodiment of the invention, following the high temperature reverse transcription incubation, the reverse transcription reaction is adjusted to PCR buffering conditions, and the amplification reaction is initiated following the addition of a second primer. PCR buffer is added to maintain the appropriate buffering capacity, pH, monovalent cation concentration, and to dilute the concentration of enzyme and dNTPs to within 20–200 $\mu$M each dNTP. MgCl$_2$ is added to a final concentration of 1–3 mM. Preferably, the concentrations of dNTPs in both the reverse transcriptase and PCR reaction mixes are balanced. Because Mn$^{+2}$ can induce hydrolysis of RNA and possibly DNA, as well as diminish PCR amplification when present at high concentrations, in a preferred embodiment of the invention the Mn$^{+2}$ is chelated prior to the PCR amplification. The presence of high amounts of Mn$^{+2}$ also may decrease fidelity during amplification, however chelating the Mn$^{+2}$ avoids this problem. Accordingly, it is preferred that following the reverse transcription reaction, EGTA is added at a concentration between about 1–10 times the molar concentration of Mn$^{+2}$ to chelate the Mn$^{+2}$. In the presence of both Mg$^{+2}$ and Mn$^{+2}$, EGTA preferentially binds Mn$^{+2}$. Low dNTP and Mg$^{+2}$ concentrations, as described herein, may also increase fidelity of Tth during amplification. Glycerol and non-ionic detergent (for example, Tween-20 TM) may be added to a final concentration of between 1–10% and 0.05%–0.01%, respectively, to increase enzyme stability.

In an alternative embodiment, Mn$^{+2}$ is not chelated prior to PCR. PCR can utilize Mn$^{+2}$ in place of Mg$^{+2}$, although Mg$^{+2}$ is preferred as described above. In particular, for applications such as, for example, large scale diagnostic screening, the risk of infidelity during amplification and low level hydrolysis of template may be tolerable in view of the tremendous advantages a homogeneous RT/PCR method provides. The two-step single addition procedure minimizes sample handling and reduces the potential for cross contamination. Because MnCl$_2$ effects PCR efficiency, the optimum concentration is preferably titrated by standard means for the particular reaction components utilized: primers, target concentration, dNTP concentration, etc. In present embodiments of a homogeneous RT/PCR assay, the optimum MnCl$_2$ concentration is approximately 0.8 mM.

The methods provided herein have numerous applications, particularly in the field of molecular biology and medical diagnostics. The reverse transcriptase activity described provides a cDNA transcript from an RNA template. The methods for production and amplification of DNA segments from an RNA molecule are suitable where the RNA molecule is a member of a population of total RNA or is present in a small amount in a biological sample. Detection of a specific RNA molecule present in a sample is greedy facilitated by a thermoactive or thermostable DNA polymerase used in the methods described herein. A specific RNA molecule or a total population of RNA molecules can be amplified, quantitated, isolated, and, if desired, cloned and sequenced using a thermoactive or thermostable enzyme as described herein.

The methods and compositions of the present invention are a vast improvement over prior methods of reverse transcribing RNA into a DNA product. When starting with an RNA template, these methods have enhanced specificity and provide templates for PCR amplification that are produced more efficiently than by previously available methods. The invention provides more specific and, therefore, more accurate means for detection and characterization of specific ribonucleic acid sequences, such as those associated with infectious diseases, genetic disorders, or cellular disorders.

Those skilled in the art will recognize that the compositions of the instant invention can be incorporated into kits. Thus, the invention relates to kits that contain a thermoactive DNA polymerase as well as instructions describing the method for using the same for reverse transcribing RNA. In one embodiment such a kit may relate to the detection of at least one specific target RNA sequence in a sample. Such a kit would comprise, in addition to the elements listed above, a primer comprising a sequence sufficiently complimentary to a specific target RNA sequence to hybridize therewith. Diagnostic kits for the amplification and detection of at least one specific RNA sequence in a sample may comprise a primer having a sequence sufficiently identical with the RNA target to hybridize with the first strand of cDNA synthesized to prime synthesis of a second cDNA strand. Kits may contain, in addition to the components listed, the four deoxyribonucleotide triphosphates, suitable buffers as described herein, oligo(dT), RNase H, linkers for cloning, as well as one or more restriction enzymes.

The following examples are offered by way of illustration only and should not be construed as intending to limit the invention in any manner.

EXAMPLE I

Materials and Methods

I. Substrates

A. RNA

RNA was synthesized in vitro using T7 RNA polymerase and a synthetic template, pAW106. The template, pAW106, contains a T7 promoter adjacent to a synthetically prepared DNA segment followed by a polyadenylation sequence. The RNA produced, referred to herein as cRNA, was purified by oligo(dT) chromatography. The purified material, 1060 bases in length, contained a portion of interleukin 1β (IL-1β) mRNA sequence. The RNA concentration was 0.1 μg/μl which was equivalent to ~0.286 pmoles/μl.

Alternatively, pAW109 (ATCC No. 68152) was used as a template to prepare cRNA, 963 bases in length. Whether pAW106 or pAW109 cRNA was used, the cRNA was prepared and quantitated according to Wang et al. supra. In some examples pAW109 cRNA was diluted to limit the number of template molecules and *E. coli* ribosomal RNA (Boehringer Mannheim) was added for a total of 60 ng of RNA/reaction.

K562, a Philadelphia-chromosome positive cell line (Lozzio and Lozzio, 1975, *Blood* 45:321–334, and Kawasaki et al., 1988, *Proc. Natl. Acad. Sci. USA* 85:5698–5702), was used as a source of total cellular RNA. The RNA was purified according to Kawasaki et al., 1985, *Science* 235:85–88, and Schwartz et al., 1981, *J. Immunol.* 126:2104–2108.

B. DNA

A DNA template was provided as a control for monitoring the activity of DNA polymerase. A solution of activated salmon sperm DNA was prepared at a concentration of 2.5 μg/μl in 10 mM Tris-HCl, pH 8.3, mM KCl, and 50 μM EDTA. One reaction contained 6.25 μm of salmon sperm DNA template (2.5 μl). In some examples pAW109 was diluted to limit the number of template molecules and *E. coli* ribosomal RNA (Boehringer Mannheim) was added for a total of 60 ng of RNA/reaction.

II. Oligonucleotide Primers

DM156 was used to prime cDNA synthesis using the pAW106 cRNA template. The primer sequence corresponds to a portion of the human IL-1β gene and is complementary to human IL-1β mRNA. The primer concentration was 100 pmol/μl.

DM152 and DM151 correspond to a portion of the human IL-1α a gene and amplify a 420 base pair segment when IL-1α mRNA (for example, from K562 cells) is used as the template. A 308 base pair segment is produced from pAW109 cRNA. DM152 hybridizes to pAW109 cRNA or IL-1α mRNA to prime cDNA synthesis. DM151 hybridizes to the single-stranded cDNA as the "upstream" amplification primer.

TM01 was used as the "downstream" primer to synthesize a cDNA molecule from the pAW109 cRNA template and can hybridize to the 3' untranslated region of human IL-1α mRNA. DM151 and TM01 amplify a 736 base pair segment of pAW109.

| | | |
|---|---|---|
| DM156 | SEQ ID NO. 9 | 5'-TGGAGAACACCACTTGTTGCTCCA |
| DM151 | SEQ ID NO. 10 | 5'-GTCTCTGAATCAGAAATCCTTCTATC |
| DM152 | SEQ ID NO. 11 | 5'-CATGTCAAATTTCACTGCTTCATCC |
| TM01 | SEQ ID NO. 12 | 5'-GCTTGCAAGCTTTATTTAGTTATGACTGATAACACTC |

III. Deoxyribonucleoside Triphosphates

The amount of reverse transcription (RT) product formed was monitored by the incorporation of α$^{32}$P dCTP. Therefore, a dNTP minus C stock was prepared comprising 2 mM dATP, 2 mM dTTP, and 2 mM dGTP. A 330 μl, 1 mM4 dCTP solution was prepared containing 100 μCi α$^{32}$P dCTP (New England Nuclear). Therefore, approximately 6.6×10$^5$ cpm represents 10$^3$ pmoles dCTP incorporated. The dNTP minus C and dCTP solutions were combined to prepare a 5X dNTP stock mix containing 1 mM dATP, 1 mM dATP, 1 mM dGTP, and 250 µM $\alpha^{32}$P dCTP. Alternatively, when no radio-labelled triphosphate is used, all four dNTPs are included in the reverse transcription reaction at 200 µM. For convenience a solution containing 2 mM each of dATP, dCTP, dGTP and dTTP in $H_2O$, pH 7.0, is prepared as a 10X stock solution. Alternatively, reverse transcription/PCR product was monitored by agarose gel electrophoresis and ethidium bromide staining.

IV. Buffers

A. Annealing Buff

The 10X stock annealing buffer was prepared containing 100 mM Tris-HCl pH 8.3, 500 mM KCl and 1 mM EDTA.

B. Modified Pol I 10X Buffer

The 10X Pol I buffers were prepared with and without $MgCl_2$ containing 100 mM Tris-HCl, pH 8.3, 500 mM KCl, 10 mM DTT, and 60 mM $MgCl_2$ if present.

C. Taq Polymerase/Reverse Transcription 10X Buffer (HSB)

The 10X In buffer was prepared containing 100 mM Tris-HCl, pH 8.3 and 500 mM KCl.

D. 10X Low Salt Buffer (LSB)

The 10X LSB was prepared containing 100 mM Tris-HCl, pH 8.3 and 50 mM KCl.

E. 10X RT Reaction Buffer

The 10X RT buffer was prepared containing 100 mM Tris-HCl (pH 8.3) and 900 mM KCl.

F. MoMuLV-RT 10X Buffer

The 10X MoMuLV-RT buffer was prepared as in C, above, with the addition of 60 mM $MgCl_2$.

G. 10X PCR Buffer

The 10X PCR buffer was prepared containing 100 mM Tris-HCl, pH 8.3, 1M KCl, 18.75 mM $MgCl_2$, 7.5 mM EGTA, and 50% glycerol (v/v).

H. 10X Tag PCR Buffer

The 10X IN PCR buffer contained 100 mM Tris-HCL (pH 8.3), 300 mM KCl, and 25 mM $MgCl_2$.

1. Taq Diluent

Taq dilution buffer was prepared comprising: 25 mM Tris-HCl, pH. 8.8, 100 mM KCl, 0.1 mM EDTA, 0.5% Tween-20 TM, 0.5% Nonidet TM P-40, and 500 µg/µl gelatin.

V. Enzymes

A. Reverse Transcriptase (MoMuLV-RT) was obtained from Bethesda Research Labs, Bethesda, Md. at a concentration of 200 µ/µl. The enzyme was diluted in Taq Diluent with 1/5 concentration of Tween-20 TM and Nonidet TM P-40 to provide 4, 0.4, 0.04, and 0.004 µ/µl preparations.

B. *E. coli* Pol I was purchased from New England Biolabs at a concentration of 10 units/µl.

C. Native Taq (94 kDa) was provided by Perkin-Elmer/Cetus at a concentration of 48 units/µl. The specific activity was approximately 240,000 units/mg. Taq diluent was used to reduce the concentration to 10 units/µl.

D. rTaq DNA Polymerase, Stoffel Fragment

The Stoffel fragment of In polymerase is a truncated form of 94 kDa Taq in which the 32 kDa amino terminal sequence has been deleted. Although the enzyme is 61 kDa in size, it has previously been referred to as 62 kDa Taq. The enzyme can be produced in and purified from recombinant host cells as described in commonly assigned, co-pending Ser. No. 143,441, incorporated herein by reference. Stoffel fragment is commercially available from Perkin Elmer Cetus Instruments as AmpliTaq TM DNA polymerase, Stoffel Fragment.

E. Tth Polymerase

Native Tth polymerase is commercially available from Finnzyme Co., Finland, and from Toyobo Co., Japan. Methods for purifying 94 kDa native Tth DNA polymerase and producing and purifying recombinant 94 kDa Tth are described in commonly assigned, co-pending Ser. No.455,967, now abandoned in favor of continuation application Ser. No. 07/880,478, filed May 6, 1992, and also published as WO91/09950, by inventors David Gelfand, Susan Stoffel, and Frances Lawyer, filed Dec. 22, 1989, and incorporated herein by reference. For use in the present examples, recombinant Tth (rTh) was purified as described below and is commercially available from Perkin Elmer Cetus Instruments.

Tth was purified from *E. coli* strain DG116 containing plasmid pLSG33. As described at page 46 of the specification of U.S. patent application Ser. No. 455,967, now abandoned in favor of continuation application Ser. No. 07/880,478, filed May 6, 1992, and also published as WO91/09950, pLSG33 was prepared by ligating the NdeI-BamHI restriction fragment of pLSG24 into expression vector pDG178. The resulting plasmid is ampicillin resistant and is capable of expressing the full-length Tth gene. The seed flask for a 10 liter fermentation contains tryptone (20 g/l), yeast extract (10 g/l), NaCl (10 g/l) and 0.005% ampicillin. The seed flask was inoculated from colonies from an agar plate, or a frozen glycerol culture stock can be used. The seed is gown to between 0.5 and 1.0 O.D. (A680). The volume of seed culture inoculated into the fermentation is calculated such that the final concentration of bacteria will be 1 mg dry weight/liter. The 10 liter growth medium contained 25 mM $KH_2PO_4$, 28 mM $(NH_4) SO_4$, 4 mM sodium citrate, 0.4 mM $FeCl_2$, 0.04 mM $ZnCl_2$, 0.03 mM $CuCl_2$, 0.03 mM $CuCl_2$, and 0.03 mM $H_3BO_3$. The following sterile components were added: 4 mM $MgSO_4$, 7.5 g/l glucose, and 20 mg/l thiamine-HCl. The pH was adjusted to 6.8 with NAOH and controlled during the fermentation by added $NH_4OH$. Glucose was continually added during the fermentation by coupling to $NH_4OH$ addition. Foaming was controlled by the addition of polypropylene glycol as necessary, as an anti-foaming agent. Dissolved oxygen concentration was maintained at 40%.

The fermentation was inoculated as described above and the culture was grown at 30° C. until an optical density of 21 (A680) was reached. The temperature was then raised to 37° C. to induce synthesis of rTth polymerase. Growth continued for eight hours after induction, and the cells were then harvested by concentration using cross flow filtration followed by centrifugation. The resulting cell paste was frozen at −70° C. and yielded about 500 grams of cell paste. Unless otherwise indicated, all purification steps were conducted at 4° C.

Approximately 280 grains of frozen 1°-70° C.) *E. coli* K12 strain DG116 harboring plasmid pLSG33 were warmed overnight to −20° C. To the cell pellet the following reagents were added: 1 volume of 2X TE (100 mM Tris-HCl, pH 7.5, 2 mM EDTA), 5 mg/ml leupeptin and 50 mg/n-d PMSF. The final concentration of leupeptin was 0.5 µg/ml and for PMSF, 0.625 µg/ml. Preferably, betamercaptoethanol (2-Me) is included in TE to provide a final concentration of 5 mM 2-Me. The mixture was homogenized at low speed in a blender. All glassware was baked prior to use, and solutions used in the purification were autoclaved, if possible, prior to use. The cells were lysed by passage twice through a Microfluidizer at 10,000 psi.

The lysate was diluted with 1X TE containing 5 mM 2-Me to a final volume of 5.5X cell wet weight. Leupeptin was added to 0.5 µg/ml and PMSF was added to 0.625 µg/ml. The final volume (Fraction 1) was approximately 1540 ml.

Ammonium sulfate was gradually added to 0.2M (26.4 g/l) and the lysate stirred. Upon addition of ammonium sulfate, a precipitate formed which was removed prior to the polyethylenimine (PEI) precipitation step, described below. The ammonium sulfate precipitate was removed by centrifugation of the suspension at 15,000–20,000 xg in a JA-14 rotor for 20 minutes. The supernatant was decanted and retained. The ammonium sulfate supernatant was then stirred on a heating plate until the supernatant reached 75° C. and then was placed in a 77° C. bath and held there for 15 minutes with occasional stirring. The supernatant was then cooled in an ice bath to 20° C. and a 10 ml aliquot was removed for PEI titration.

PEI titration and agarose gel electrophoresis were used to determine that 0.3% PEI (commercially available from BDH as PolyminP) precipitates ≧90% of the macromoleculer DNA and RNA, i.e., no DNA band was visible on an ethidium bromide stained agarose gel after treatment with PEI. PEI was added slowly with stirring to 0.3% from a 10% stock solution. The PEI treated supernatant was centrifuged at 10,000 RPM (17,000 xg) for 20 minutes in a JA-14 rotor. The supernatant was decanted and retained. The volume (Fraction II) was approximately 1340 ml.

Fraction II was loaded onto a 2.6×13.3 cm (71 ml) phenyl sepharose CL-4B (Pharmacia-LKB) column following equilibration with 6 to 10 column volumes of TE containing 0.2M ammonium sulfate. Fraction II was then loaded at a linear flow rate of 10 cm/hr. The flow rate was 0.9 ml/min. The column was washed with 3 column volumes of the equilibration buffer and then with 2 column volumes of TE to remove non-Tth DNA polymerase proteins. The column was then washed with 2 column volumes of 20% ethylene glycol in TE to remove additional contaminating proteins. The recombinant Tth was eluted with 4 column volumes of 2.5M urea in TE containing 20% ethylene glycol. The DNA polymerase containing fractions were identified by optical absorption ($A_{280}$) and SDS-PAGE according to standard procedures. Peak fractions were pooled and filtered through a 0.2 micron sterile vacuum filtration apparatus. The volume (Fraction III) was approximately 195 ml. The resin was equilibrated and recycled according to the manufacturer's recommendations.

A 2.6×1.75 cm (93 ml) heparin sepharose Cl-6B column (Pharmacia-LKB) was equilibrated with 6–10 column volumes of 0.15M KCl, 50 mM Tris-HCl, pH 7.5, 0.1 mM EDTA and 0.2% Tween 2 TM, at 1 column volume/hour. Preferably, the buffer contains 5 mM 2-Me. The column was washed with 3 column volumes of the equilibration buffer. The Tth polymerase was eluted with a 10 column volume linear gradient of 150–750 mM KCl gradient in the same buffer. Fractions (one-tenth column volume) were collected in sterile tubes and the peak was determined as for Fraction III. Recombinant Tth polymerase eluted with a peak at 0.33M KCl. The peak fractions were pooled (Fraction IV, volume 177 ml).

Fraction IV was concentrated to 10 ml on an Amicon YM30 membrane. For buffer exchange, diafiltration was done 5 times with 2.5X storage buffer (50 mM Tris-HCl, pH 7.5, 250 mM KCl, 0.25 mM EDTA 2.5 mM DTT and 0.5% Tween-20 TM) by filling the concentrator to 20 ml and concentrating the volumes to 10 ml each time. The concentrator was emptied and rinsed with 10 ml 2.5X storage buffer which was combined with the concentrate to provide Fraction V.

Anion exchange chromatography was used to remove residual DNA. The procedure was conducted in a biological safety hood and sterile techniques were used. A Waters Sep-Pak plus QMA cartridge with a 0.2 micron sterile disposable syringe tip filter unit was equilibrated with 30 ml of 2.5X storage buffer using a syringe at a rate of about 5 drops per second. Using a disposable syringe, Fraction V was passed through the cartridge at about 1 drop/second and collected in a sterile tube. The cartridge was flushed with 5 ml of 2.5 ml storage buffer and pushed dry with air. The eluant was diluted 1.5 X with 80% glycerol and stored at −20° C. The resulting final Fraction IV pool (57.5 mls) contained $16.1 \times 10^6$ units of activity.

VI. Annealing Procedure

For Examples II, III, and IV the cRNA template and DM156 primer were annealed at a 20:1 primer template ratio in 10 mM Tris HCl, pH 8.3, 50 mM KCl, 0.1 mM EDTA annealing buffer. To reduce pipeting errors and eliminate tube variations, a master mix was made to provide material for 80 reactions.

Annealing was accomplished as follows: the 80 reaction master mix was heated to 85°–87° C. for 4 minutes, then placed in a 70° C. water bath for 5 minutes, followed by a 60° C. water bath for 5 minutes and finally allowed to equilibrate at room temperature. The annealed mixture was then stored at 4° C. (or alternatively at −20° C.) for future use. For each reaction 2.5 µl of master mixture was used containing 0.5 pmol (0. 175 µg) cRNA template and 10 pmoles primer. Alternatively, annealing was accomplished at 70° C. during incubation of the RT reaction.

VII. Determination of $\alpha^{32}$PdCTP Incorporation

The amount of isotope incorporated in the reverse inscribed product was measured by nucleic acid precipitation with trichloroacetic acid (TCA). This method is described in Maniatis et al., 1982, *Molecular Cloning*, Cold Spring Harbor Laboratory, page 473.

EXAMPLE II

Analysis of AW106 cRNA as a Suitable Template for Reverse Transcription

The annealed AW 106 cRNA:DM156 mixture was used as a template for reverse transcription with commercially available reverse transcriptase to test the suitability of AW106 cRNA as a template.

A 6X reaction mix was prepared containing 1X Pol I RT Buffer plus $MgCl_2$, 1X dNTP Stock, and 3 pmoles template annealed to 60 pmoles primer. This mix was aliquoted into six tubes. All reactions were set up at 0° C. As controls, one reaction was set up without template but with 10 units of MoMuLV-RT. Another reaction had no enzyme added. To the remaining reactions, MoMuLV-RT was added as follows: 10 units, 1 unit, 0.1 unit, and 0.01 unit.

All reactions were incubated at 37° C. for 20 minutes. The reactions were stopped by placing them in a 0° C. water ice/bath and adding EDTA to a final concentration of 10 mM. The $\alpha^{32}$PdCTP incorporation was determined by measuring TCA precipitable counts.

The results demonstrated that AW106 cRNA was a suitable template for cDNA synthesis using MoMuLV-RT.

EXAMPLE III

Comparison of *E. coli* Pol I and Taq Reverse Transcriptase Activities

Using the results of Example n as a standard, *E. coli* Pol I and nTaq polymerase were assayed for reverse transcriptase activity using AW106 cRNA as a template. As positive controls, DNA templates were substituted for the cRNA template in one set of reactions. The results were quantitated as in Example II by measurement of $\alpha^{32}$PdCTP incorporation.

A 12X Pol I master mix was prepared containing Pol I RT buffer minus MgCl$_2$ dNTP stock and 12 units Pol I enzyme. Similarly, a 12X Taq master mix was prepared containing IU buffer, dNTP stock, and 12 units of native Taq enzyme and Taq diluent. The Pol I and Taq master mixes were divided to provide six reactions for the RNA template (0.5 pmoles cRNA/10 pmole DM156), two reactions for the DNA template (6.25 μg), and two control reactions with no template.

For the RNA template MnCl$_2$ or MgCl$_2$ was added to the six aliquots containing Pol I master mix plus cRNA/DM156 to achieve salt concentrations of 0, 0.5 mM MnCl$_2$, 0.7 mM MnCl$_2$, 1.0 mM MnCl$_2$, 2.0 mM MnCl$_2$, and 6 mM MgCl$_2$. Six aliquots containing in master mix plus cRNA/DM156 were supplemented with MnCl$_2$ or MnCl$_2$ so that the final salt concentration was 0, 0.5 mM MnCl$_2$, 0.7 mM MnCl$_2$, 1.0 mM MnCl$_2$, 2.0 mM MnCl$_2$, or 2 mM MgCl$_2$.

For the DNA template two aliquots were removed from the Pol I mix, and salt was added as to provide a final concentration of 0.7 mM MnCl$_2$ for one reaction and 6 mM MgCl$_2$ for the other. Two aliquots were removed from the Taq mix, and salt was added to provide a final concentration of 0.7 mM MnCl$_2$ for one reaction and 2 mM MgCl$_2$ for the other.

As negative controls, two reaction mixes were prepared for each of Pol I and Taq which lacked a template. These reactions were assembled using aliquots of the 12X Pol I and 12X Taq master mixes, and 1X annealing buffer was added in place of a template. For Pol I, salt was added to provide either 0.7 mM MnCl$_2$ or 6 mM MgCl$_2$. For Taq, salt was added to provide either 0.7 mM MnCl$_2$ or 2 mM MgCl$_2$.

All reactions were mixed on ice and then incubated at 37° C. for Pol I or at 65° C. for Taq. After 20 minutes the reactions were chilled on ice (0° C.) and EDTA was added to each reaction to a 10 mM final concentration. A sample was removed from each reaction to measure $\alpha^{32}$PdCTP incorporation.

The results of this experiment are shown in Table I. All values shown are corrected for background.

TABLE I

| | MoMuLV-RT (cpm) | nTaq (cpm) | *E. coli* Pol I (cpm) |
|---|---|---|---|
| minus template + 10 units enzyme | 90 | — | — |
| minus enzyme + template | 14 | — | — |
| 10 units enzyme + template | 7,825 | — | — |
| 1 unit enzyme + template | 3,263 | — | — |
| .1 unit enzyme + template | 924 | — | — |
| .01 unit enzyme + template | 170 | — | — |
| RNA template + 0 mM MnCl$_2$ | — | 9 | 0 |
| RNA template + .5 mM MnCl$_2$ | — | 256 | 7,561 |
| RNA template + .7 mM MnCl$_2$ | — | 3,088 | 6,666 |
| RNA template + 1 mM MnCl$_2$ | — | 3,977 | 7,508 |
| RNA template + 2 mM MnCl$_2$ | — | 2,696 | 1,558 |
| RNA template + 2mM MnCl$_2$ | — | 73 | — |
| RNA template + 6 mM MnCl$_2$ | — | — | 760 |
| minus template + 6 mM MnCl$_2$ | — | — | 31 |
| minus template + .7 mM MnCl$_2$ | — | 5 | 28 |
| minus template + 2 mM MnCl$_2$ | — | 3 | — |
| DNA template + .7 mM MnCl$_2$ | — | 194,199 | 203,861 |
| DNA template + 6 mM MnCl$_2$ | — | — | 271,595 |
| DNA template + 2 mM MnCl$_2$ | — | 209,559 | — |

The data presented in Table I is presented graphically in FIG. 1. This experiment demonstrates that Taq has reverse transcriptase activity. One unit of Taq is equivalent to 1 unit of MoMuLV reverse transcriptase by the amount of $\alpha^{32}$PdCTP incorporated into a DNA transcript from an RNA template. *E. coli* Pol I also shows reverse transcriptase activity. Because Taq reactions were dome at 65° C. rather than 37° C., product specificity is enhanced in the Taq reaction compared to either the Pol I or MoMuLV reverse transcriptase.

EXAMPLE IV

Comparison of Reverse Transcriptase Activity in 94 kDa rTaq, 62 kDa rTaq and Tth Polymerase In order to determine whether the reverse transcriptase activity observed in Example III was common to other thermostable polymerases, the reverse transcription activity of 94 kDa Taq polymerase, Stoffel fragment (previously referred to as 62 kDa Taq), and native Tth were compared. Both forms of Taq were produced by recombinant means.

A 2 μM dilution of 94 kDa Taq was prepared, assuming 94 μg/mnole, from a 23.4 μM stock solution. A dilution of the Stoffel fragment was similarly prepared using Taq diluent.

Both the 94 kDa and Stoffel fragment dilutions contained, 0.36 pmoles/0.18 μl. Tth polymerase was purified as a 27 unit/μl solution with a specific activity of 80,000 units/mg. Therefore, 0.1 μl contained 0.36 pmole (2.7 units of enzyme). Reaction were set up with a final salt concentration of 60 mM KCl (HSB) or 15 mM KCl (LSB).

At 0° C. three 15X master mixes were prepared containing dNTP stock, enzyme diluent, and 5.4 pmoles enzyme (Tth, 94 kDa Taq, or Stoffel Fragment). From each 15X master mix six aliquots were combined with either HSB or LSB providing six reaction mixes for each of Tth/HSB, Tth/LSB, 94 kDa Taq/HSB, 94 kDa Taq/LSB, Stoffel Fragment/HSB and Stoffel Fragment/LSB.

For each of the six reaction mixes two separate aliquots were removed to tubes containing 1X annealing buffer for the minus template plus enzyme control reactions.

To the remaining five reactions worth of reaction mix, cRNA/DM156 annealed mix (3 pmoles template and 60 pmoles primer) was added. From each of the six series, four aliquots were removed to individual tubes. While still at 0° C., MnCl$_2$ was added to provide the final salt concentration show in Table II.

To determine background levels, minus-enzyme, minus-template controls were prepared containing 1X dNTP stock, 1X Annealing buffer, and 0.1X Taq diluent. The salts were adjusted as follows: HSB and a final MnCl$_2$ concentration of 0.6 mM or 1.2 mM, and LSB and a final MnCl$_2$ concentration of 0.6 mM or 1.2 mM.

All reaction mixes were, incubated at 65° C. for 15 minutes. The tubes were then quenched in an ice bath and EDTA was added to each tube to a 10 mM final concentration. The amount of $\alpha^{32}$PdCTP incorporation was determined by TCA precipitation. The results are shown in Table II.

is described in Example 1(A). This embodiment of the invention excludes the pre-annealing step described in Example II and used in Examples III and IV.

The components for the RT reaction were combined at room temperature, in the following order: 9.4 μl, H$_2$O; 2 μl, 10X RT Reaction Buffer (100 mM Tris HCl (pH 8.3),900 mM KCl); 2 μl, 10 mM MnCl$_2$; 1.6 μl, dNTP solution (2.5 mM each dATP, dCTP, dGTP, dTTP in H$_2$O at pH 7.0); and 2 rTth DNA polymerase (2.5 units/μl in 1X enzyme storage buffer containing 20 mM Tris-HCl [pH 7.5], 100 mM KCl. 0.1 mM EDTA 1 mM DTT, 0.2% Tween20 TM [Pierce Surfactamps] and 50% glycerol v/v]). Although the indicated volumes shown are intended as per reaction, for consistency and to avoid pipeting errors, the RT reaction mix was prepared as a 25X master mix. The 25X on master contained 425 μl (17 μl/Reaction).

RT-Primer mixes were prepared each as follows. 187 μl of RT mix was removed from the 25X RT master mix and combined with a "downstream" primer. This amount was sufficient for 11 RT reactions. Two RT-Primer mixes were prepared each containing 187 μl RT reaction mix and 11 μl (1 μl per reaction) of either 15 μM DM152 (in water); or 15 μM TM01 (in water).

TABLE II

|  | 94 kDA rTaq | | Stoffel Fragment (62 kDa Taq) | | Tth Pol | |
| --- | --- | --- | --- | --- | --- | --- |
|  | cpm | pMoles | cpm | pMoles | cpm | pMoles |
| HSB |  |  |  |  |  |  |
| Minus template + 0.6 mM MnCl$_2$ | 0 | — | 0 | — | 10 | — |
| Minus template + 1.2 mM MnCl$_2$ | 0 | — | 0 | — | 6 | — |
| Plus template + 0.6 mM MnCl$_2$ | 517 | 5.04 | 34 | 0.332 | 1244 | 12.14 |
| Plus template + 0.8 mM MnCl$_2$ | 918 | 8.96 | 340 | 3.32 | 1981 | 19.33 |
| Plus template + 1.0 mM MnCl$_2$ | 1315 | 12.83 | 521 | 5.08 | 2178 | 21.25 |
| Plus template + 1.2 mM MnCl$_2$ | 1305 | 12.73 | 609 | 5.9 | 2369 | 23.11 |
| LSB |  |  |  |  |  |  |
| Minus template + 0.6 mM MnCl$_2$ | 7 | — | 0 | — | 234 | 2.28 |
| Minus template + 1.2 mM MnCl$_2$ | 18 | — | 0 | — | 2 | — |
| Plus template + 0.6 mM MnCl$_2$ | 276 | 2.69 | 81 | 0.79 | 618 | 6.03 |
| Plus template + 0.8 mM MnCl$_2$ | 1115 | 10.88 | 468 | 4.57 | 2263 | 23.06 |
| Plus template + 1.0 mM MnCl$_2$ | 1349 | 13.16 | 1068 | 10.46 | 2239 | 21.85 |
| Plus template + 1.2 mM MnCl$_2$ | 1061 | 10.35 | 898 | 8.76 | 2051 | 20.01 |
| Controls |  |  |  |  |  |  |
| Minus Enzyme, Minus Template Reactions | cpm |  |  |  |  |  |
| 60 mM KCl .6 mM MnCl$_2$ | 19 |  |  |  |  |  |
| 60 mM KCl 1.2 mM MnCl$_2$ | 46 |  |  |  |  |  |
| 15 mM KCl .6 mM MnCl$_2$ | 11 |  |  |  |  |  |
| 15 mM KCl 1.2 mM MnCl$_2$ | 25 |  |  |  |  |  |

Input $^{32}$P for each reaction was 1.23×10$^6$ cpm. All numbers were corrected for average background of 37 cpm. The numbers reflect cpm incorporated per 12.5 μl of each reaction. Total pmoles of incorporation was calculated based on 984 cpm/pmole determined by counting $^{32}$P from an $\alpha^{32}$p-dCTP stock solution.

These results are presented graphically in FIG. 2 and demonstrate that all thermostable DNA polymerases tested contain reverse transcriptase activity.

EXAMPLE V

Procedure for High Temperature Reverse Transcription/Amplification

Examples III and IV demonstrate the ability of thermostable DNA polymerases to use an RNA template and produce a cDNA molecule, at an elevated temperature. In this experiment, the reverse transcriptase reaction was coupled to cDNA amplification by PCR. Recombinant Tth was used as the thermostable polymerase for both the reverse transcriptase reaction and PCR. The cRNA template, prepared from plasmid pAW109

Aliquotes comprising 18 μl of the DM152 RT-Primer mix were removed into tubes labeled 1-8. Similarly, 18 μl aliquotes of the TM01 RT-Primer mix were removed into tubes numbered 9-16.

Template AW109 cRNA was prepared as described in Example 1, diluted, and added as a 2 μl template solution in TE (10 mM Trim-HCl, 1 mm EDTA), as shown below. The template solution contained 30 ng/μl rRNA as carrier.

| Tube Number | Copies of AW109 cRNA |
| --- | --- |
| 1, 9 | 10$^8$ (−RT reaction) |
| 2, 10 | 10$^8$ |
| 3, 11 | 10$^6$ |
| 4, 12 | 10$^4$ |
| 5, 13 | 10$^3$ |
| 6, 14 | 500 |
| 7, 15 | 100 |
| 8, 16 | 0 |

Reaction tubes 2-8 and 10-16 were incubated at 70° C. for 2.5 minutes for DM152 and 7.5 minutes for TM01 samples. Tubes 1 and 9 were kept on ice as RT reaction negative controls to detect the presence of contaminating plasmid DNA that could later serve as a PCR template. After incubation at 70° C., the reactions were stopped by placing the tubes on ice.

The PCR assay mix was prepared at room temperature as a 19X master mix. The volumes shown are intended as volume per reaction: 71 µl H2O; 8 µl 10X PCR Reaction Buffer (100 mM Tris-HCl [pH 8.3]; 1M KCl, 18.75 MM MgCl2; 7.5 mM EGTA; 50% glycerol [v/v]) and 1 µl, 15 µM DM151 (the "PCR upstream primer"). The total volume was 80 µl per reaction.

The PCR amplification was initiated by adding the 80 µl PCR assay mixture to the 20 µl reverse transcriptase reaction. A mineral oil overlay (75 µl) was added to prevent evaporation and the mix was then spun in a microcentrifuge for approximately 20 seconds to separate the oil layer from the reaction mix. PCR was conducted using a Perkin Elmer Cetus Instruments Thermal Cycler and four linked files as follows:

File 1—Step Cycle 2 minute at 95° C. for 1 cycle
File 2—Step Cycle 1 minute at 95° C. and 1 minute at 60° C. for 35 cycles
File 3—Step Cycle 7 minute at 60° C. for 1 cycle
File 4—Soak 4° C.

Following PCR, 5 µl aliquots were removed from each sample and combined with 5 µl sample dye (30% w/v sucrose, 0.1% w/v bromophenol blue, 10 mM EDTA) analyzed on an agarose-gel (2% Nu Sieve® GTG agarose [FMC], 1% Seakem® ME agarose [FMC]). Following electrophoresis, the gel was stained with ethidium bromide and photographed (see FIG. 3). AH product lengths were determined relative to a 1 kb BRL molecular weight standard (lane not shown). In the figure, the lane numbers correspond to tube numbers. The expected product, 308 bp in length, was visible at 100 copies AW109 cRNA per reaction. When TM01 was used to produce a 730 base pair transcription/amplification product, the correct size band was visible at 100 molecules of template per reaction. No PCR product was detected in the negative control reactions.

EXAMPLE VI

Coupled Reverse Transcription/Amplification Using Total Cellular RNA

The K562 cell fine was used as a source of total cellular RNA. The RNA was purified as described in Example I. The purpose of this experiment was to examine the sensitivity of the coupled RT/PCR procedure using a naturally occurring heterogenous RNA composition. Generally, it can be assumed that 250 ng of total RNA per reaction represents approximately 25,000 cells. Each cell contains approximately 1-10 copies of IL-1α mRNA. Therefore, 250 ng of K562 total RNA contains roughly 25,000 to 250,000 copies of IL-1α target mRNA. Thus, the specificity and amount of PCR product can be compared to the specificity and amount of product made using the synthetic cRNA template in Example V.

The reaction conditions were as described in Example V using DM151 and DM152 with a few minor changes described below. Because only one downstream primer was used in this experiment, DM152 was added directly to the RT reaction mix. A 10X RT reaction master mix was prepared containing, for each reaction, 9 µl H2O; 2 µl 10X RT Reaction Buffer; 2 µl 10 mM MnCl2; 2 µl dNTP (2 mM each dATP, dCTP, dGTP, and dTFP in H2O, pH 7.0) and 1 µl DM152 (15 µl in water). The RT master mix was prepared at room temperature and 16 aliquots were dispensed into tubes numbered 1-9 containing RNA as shown below.

| Tube Number | K562 Total RNA |
|---|---|
| 1 | 250 ng (−RT control) |
| 2 | 250 ng |
| 3 | 50 ng |
| 4 | 10 ng |
| 5 | 2 ng |
| 6 | 0.4 ng |
| 7 | 0.08 ng |
| 8 | 0 ng |

All template solutions were in TE (10 mM Trim-HCl, 1 mM EDTA). Two µl of template solution and 2 µl of Tth polymerase (2.5 units/µl in 1X enzyme storage buffer) were added to each tube.

All samples were incubated at 70° C. for 2.5 minutes with the exception of tube 1 which was kept on ice as a negative RT control to test for the presence of contaminating DNA that might serve later as a PCR template. The reactions were stopped by placing them on ice.

The PCR assay mix was prepared, and the reaction was carried out exactly as described in Example V. The RT/PCR insults were, analyzed as in Example V, and the results are shown in FIG. 4. A PCR product band was visible in lanes 2-7. The results, shown in FIG. 4, demonstrate that as little as 80 picograms of total cellular RNA (corresponding to 8-80 cell equivalents of RNA) serves as an excellent template for specific and efficient high temperature reverse transcription and amplification according to the methods of the present invention.

EXAMPLE VII

Procedure for High Temperature Reverse Transcription/Amplification Wherein the Polymerase is Exchanged Example IV suggests that Tth polymerase may be superior to Taq polymerase for preparing cDNA. However, Taq polymerase is frequently used in PCR. Therefore, a procedure was developed wherein Tth polymerase catalyzes the RT reaction and Taq polymerase catalyzes PCR. The following procedure is suitable when the two reactions are catalyzed by different thermostable DNA polymerases or when the amount of polymerase in the RT reaction is decreased for PCR.

As an illustration, the following experiment was carried out. Generally, the RT reaction was carried out as in Example V, however, for half of the reaction tubes, the Tth was heat killed and replaced with Taq for PCR.

The specific protocol was as follows. The RT master mix was prepared, with DM152, exactly as described in Example VI. The RT master mix was made up as a 9X mix. Sixteen µl aliquots were removed into tubes numbered 1-8 containing AW109 cRNA or pAW109 DNA as shown below.

Template solutions were all prepared as 2 µl samples in TE as in Example V. Two µl of rTth was added to each of tubes 1-8 (2.5 units/µl in 1X enzyme storage buffer) and the RT reactions were incubated at 70° C. for 2.5 minutes, with the exception of tubes 1, 2, 5, and 6. These tubes were kept on ice as RT reaction negative controls. The reactions were stopped by placing the tubes on ice. The table below summarizes the reaction conditions for each tube.

| Lane | Sample | Reaction | Enzyme |
|---|---|---|---|
| 1 | $10^4$ copies DNA | −RT | −Taq |
| 2 | $10^4$ copies cRNA | −RT | −Taq |
| 3 | $10^4$ copies cRNA | +RT | −Taq |
| 4 | — | +RT | −Taq |
| 5 | $10^4$ copies DNA | −RT | +Taq |
| 6 | $10^4$ copies cRNA | −RT | +Taq |
| 7 | $10^4$ copies cRNA | +RT | +Taq |
| 8 | — | +RT | +Taq |

At room temperature, two PCR master mixes were prepared. PCR minus in contained, per reaction, 71 μl $H_2O$, 8 μl, 10X PCR reaction buffer (100 mM Tris-HCl, pH 8.3; 1M KCl; 18.75 $MgCl_2$, 7.5 mM EGTA, 50% glycerol [w/v]) and 1 μl DM151 (15 μM in water). The PCR minus Taq mix was prepared as a 5X solution. A PCR plus Taq master mix was also prepared as a 5X solution containing, per reaction, 68.5 μl $H_2O$; 8 μl 10X Taq-PCR reaction buffer (100 mM Tris-HCl, pH 8.3; 300 mM KCl; 25 mM $MgCl_2$), 1 μl DM151, and 0.5 μl AmpliTaq ™ (5 units/μl).

Eighty μl of PCR minus Taq master mix were added to tubes 1-4. EGTA (2 μl of 30 mM stock) was added to tubes 5-8. Mineral oil was then added to all tubes (75 μl/tube). Tubes 5-8 were heated to 99° C. for 4 minutes, and 78 μl of PCR plus Taq reaction mix was added to those tubes only (below the oil level). AU tubes were spun in a microcentrifuge for approximately 20 seconds and incubated in a thermocycler using the four linked files described in Example V. The RT/PCR amplifications were analyzed by electrophoresis as described in Example V, and the gel was photographed (FIG. V). FIG. V demonstrates that replacement of rTth with AmpliTaq ™ in PCR step does not effect product yield.

EXAMPLE VIII

Comparison of Taq Polymerase and Tth Polymerase in a Coupled RT/PCR Reaction

The use of the cRNA standard described in Example VII facilitates direct analysis of the effect of experimental conditions on RT/PCR efficiency, because the number of target molecules present in the reaction mix is known. Specifically, the efficiency of Tth and Taq polymerases in a coupled RT/PCR reaction were compared. AmpliTaq ™ DNA polymerase (330 units/μl) and rTth (1697 units/μl) were provided by Perkin Elmer Cetus Instruments. The enzymes were diluted to 2.5 units/μl in storage buffer (20 mM Tris-HCl, [pH 7.5], 100 mM KCl, 50% glycerol [v/v], 0.1 mM EDTA, 1 mM dithiothreitol and 0.2% Tween 20).

RT reactions (20;il) contained 10 mM Tris-HCl, pH 8.3; 90 mM KCl (40 mM for reactions containing Taq); 1.0 mM $MnCl_2$, 200 μM each of dATP, dCTP, dGTP, and dTTP; 15 pmol of DM152 and 5 units of rTth or Taq and $10^6$, $10^5$, or $10^4$ copies of pAW109 cRNA. The six reactions were overlaid with 75 mineral oil and incubated for 15 minutes 70° C.

Following the RT reaction, 80 μl of a solution containing 10 mM Tris-HCl, pH 8.3, 100 mM KCl, (50 mM for reactions containing Taq) 1.88 mM $MgCl_2$, 0.75 mM EGTA; 5% glycerol [v/v] and 15 pmol of primer DM151 was added. The samples (100 μl) were then amplified in a Perkin Elmer Cetus Instruments Thermal Cycler as follows: 2' at 95° C. for 1 cycle; 1' at 95° and 1' at 60° C. for 35 cycles; and 7' at 60° C. for 1 cycle. Aliquots (5 μl) of the PCR amplifications were analyzed by electrophoresis on 2% (w/v) NuSeive ® 1% (w/v) Seakem ® agarose stained with ethidium bromide.

Results

The rTth polymerase generated a 308 bp product visualized by ethidium bromide stained gel electrophoresis starting with 104 copies of target cRNA. Product was not observed for the Taq polymerase at $10^4$ or $10^5$ copies of target, although lower limits of detection would be expected if hybridization techniques were used rather than ethidium bromide staining. These results demonstrated that under similar reaction conditions the Tth polymerase provides approximately 100-fold greater sensitivity than the analogous Taq polymerase in a coupled reverse transcription PCR amplification.

EXAMPLE IX

Preferred Non-Homogeneous Reverse Transcription/PCR Protocol

A. Reverse Transcription Reaction

In a 0.5 ml polypropylene microcentrifuge tube combine 9.4 ml sterile distilled water, 2 μl 10X rTth RT buffer, 2 μl $MnCl_2$ (10 mM); 0.4 μl of each of dGTP, dATP, dTTP, and dCTP (each at 10 mM); 2 μrTth polymerase 2.5 U/μl; 1 μl of primer DM152 (15 μM) (or an alternative "downstream" primer); and 2 μl positive control RNA or experimental sample containing ≦250 ng total RNA.

In this embodiment, the positive control RNA serves a template for DM152. The control RNA concentration is preferably $\sim 10^4$ copies/20 μl. For example, the control RNA may be RNA transcribed from pAW109 in 30 μg/ml E. coli rRNA in 10 mM Tris-HCl, pH 8.0, 1 mM EDTA and 10 mM NaCl.

The total reverse transcription reaction volume should be 20 μl per sample.

To reduce evaporation or refluxing, overlay the mix with 50-100 μl mineral oil.

Incubate the tubes in a Perkin-Elmer Cetus DNA Thermal Cycler using a soak file at 70° C. for 5-15 minutes. Stop the reaction by placing the tubes on ice until needed.

B. PCR Reaction

For each sample prepare a minimum of 80 μl of PCR master mix as follows: 8 μl, 10 X chelating buffer, 6-10 μl 25 mM $MgCl_2$, 1 μl primer DM151 (15 μM) or experimental "upstream" primer and sterile distilled water. Any combination of water, $MgCl_2$ and "upstream" primer volumes can be used as long as the total volume of the master mix equals 80 μl per sample.

The optimal $MnCl_2$ concentration may vary, depending on the total dNTP concentration, and the primer and template used. In most cases a final concentration of $MgCl_2$ in the range of 1.5-2.5 mM in the reaction mix wig provide excellent results. If the template used is the positive control pAW109 RNA, 6 μl (1.5 mM) of $MnCl_2$ is preferred.

Dispense 80 μl of the PCR master mix into each reverse transcription reaction tube. Change pipet tips between additions to avoid sample carryover. Centrifuge the tubes for $\sim 30$ seconds in a microcentrifuge.

For amplification of the pAW109 RNA positive control, the Perkin Elmer Cetus DNA Thermal Cycler is programmed for four linked files as follows:

Step Cycle: 2 minutes at 95° C. for 1 cycle
Step Cycle: 1 minute at 95° C. and 1 minute at 60° C. for 35 cycles
Step Cycle: 7 minutes at 60° C. for 1 cycle
Soak: 4° C.

The PCR amplified samples can be stored frozen until subsequent analysis.

The selection of 60° C. for the anneal-extend temperature is optimal for amplification of the positive control cDNA. It may be necessary to lower or raise the anneal-extend temperature for other primer-template pairs. Higher anneal-extend temperatures generally result in a specific product (see Saiki et al., 1988, *Science* 239:487–491). The optimum can be determined empirically by testing at 5° C., or smaller, increments until the maximum in specificity and product yield is reached.

The optimal magnesium chloride concentration for PCR amplification can be determined empirically by testing concentrations from 1.5 to 2.5 mM magnesium chloride for each primer set. Too little or too much magnesium chloride may effect amplification efficiency. It may be preferable to adjust the magnesium chloride concentration in parallel with substantial changes in the concentration of sample RNA, dNTPs, cDNA, and DNA.

For templates known to contain a high amount of secondary structure, a "hot start" protocol may be preferred. Two reaction mixes for the reverse transcription reaction are prepared. Mix A: 9.4 µl sterile distilled water, 2 µl 10X rTth reverse transcriptase buffer, 1 µl "downstream primer," 2 µl sample RNA (<250 ng of total RNA). Mix B: 2 µl, 10 mM $MnCl_2$ solution; 0.4 µl dGTP; 0.4 µl dATP; 0.4 µl dCTP; 0.4 µl dTTP; 2 µl rTth DNA polymerase.

Prepare both reaction mixes at room temperature. Incubate Mix A for 5 minutes at 70° C., add reaction Mix B (while reaction Mix A is still at 70° C.) and incubate for 5 to 15 minutes at 70° C. as described above in the section entitled "Reverse Transcription Reaction." Run the PCR reaction as described above.

C. Reagents

The preferred protocol utilizes the following reagents:

| | |
|---|---|
| rTth DNA polymerase | 2.5 Units/µl |
| Primer DM152 | 15 µM |
| Primer DM151 | 15 µM |
| Positive Control RNA | $5 \times 10^3$ copies/µl |
| dATP | 10 mM |
| dGTP | 10 mM |
| dCTP | 10 mM |
| dTTP | 10 mM |
| 10X rTth Reverse Transcriptase RT Buffer: | 100 mM Tris-HCl pH 8.3, 900 mM KCl |
| 10X Chelating Buffer: | 50% glycerol (v/v) 100 mM Tris HCl, pH 8.3 1M KCl, 7.5 mM EGTA, 0.5% Tween 20 |
| $MnCl_2$ Solution | 10 mM |
| $MgCl_2$ Solution | 25 mM |

These components may be assembled as a kit for high temperature reverse transcription. Variations to the kit are within the scope of the disclosed invention. For example, $MnCl_2$ may be included in the reverse transcriptase buffer and $MnCl_2$ may be included in the Chelating buffer. However, for optimization of the reactions $MnCl_2$ and $MgCl_2$ are provided as separate reagents. The use of a positive control, while not essential, is preferred in a commercial embodiment of the invention.

EXAMPLE X

Homogeneous RT/PCR Assay

This method provides a procedure for a two-step, single addition reverse transcription/PCR reaction. A TC 9600 thermocycler (Perkin Elmer Cetus Instruments) was used and the instrument was turned on, to preheat the cover, prior to preparing the reaction mixture. In a 0.2 ml MicroAmp ® tube (Perkin Elmer Cetus Instruments), each contained 6.4 µl sterile distilled $H_2O$; 2 µl 10X RT buffer (100 mM Tris-HCl, pH 8.3; 900 mM KCl); 1.6 µl of 10 mM $MnCl_2$; 2 µl of 10X dNTP-T (2 mM each dATP, dCTP, dGTP in $H_2O$ pH 7.0); 2 µl of 2 mM dTTP; 1 µl of primer DM152 (15 µM); 1 µl of primer DM151 (15 µM); and 2 µl rTth (2.5 U/µl). A 20X reaction mixture was made up (360 µl total volume) and 18 µl mixture was aliquoted into 16 tubes containing template as described below. The template used was AW109 cRNA. Tube Nos. 1-3 and %.9-11 contained $10^4$ copies of template in 2 µl. Tube Nos. 4-6 and 12-14 each contained $10^2$ copies in 2 µl. Tube Nos. 7, 8, 15, and 16 contained only 2 µl of 30 ng/µl rRNA as a negative control.

Tube Nos. 1-8 were kept on ice during the RT reaction as −RT controls. Tube Nos. 16 were placed in a TC9600 thermocycler and heated for 1 cycle at 70° C. for 15' and then heated to 95° C. while Tube Nos. 1-8 were placed in the thermocycler for the PCR step. All tubes were cycled as follows:

75 seconds 95° C. I cycle
30 seconds 95° C., 20 seconds 60° C. for 35 cycles
2 minutes 60° C. 1 cycle Results Five µl of each reaction was then analyzed on a 2% NuSieve 1% agarose gel, strained with ethidium bromide and photographed. No product of the predicted size was visible in the −RT controls (Tube Nos. 1-8) or the "no target controls" (Tube Nos. 15 and 16). Product of the expected size was readily visible in lanes 9-11 ($10^4$ copies of target) and also present in lanes 12-14, although, expectedly, with less intensity.

EXAMPLE XI

Utilization of dUTP and Uracil-N-Glycosylase (UNG) as a PCR Carryover Prevention During High Temperature Reverse Transcription and Amplification This example frustrates the incorporation of an unconventional nucleotide to minimize carryover contamination. The reaction mix was treated with UNG prior to reverse transcription to degrade contaminating products from previous assays containing the same unconventional nucleotide. UNG treatment is as follows: 0.5 units UNG (Perkin Elmer Cetus Instruments) per 20 µl RT reaction. The reaction was incubated for 10 minutes at room temperature followed by heating at 70° C. for 15 minutes to denature the glycosylase and allow for reverse transcription. The experiment also demonstrates $MnCl_2$ concentration titration for determining the optimum concentration for the particular target, primers, and reaction conditions shown. The cDNA is then amplified by a PCR.

An 8X RT reaction mixture was prepared that contained: 48 µl sterile DEPC-treated distilled water; 16 µl 10X RT Buffer (100 mM Tris-HCl, pH 8.3; 900 mM KCl); 16 μl of a dNTP mix containing 2 mM each of dATP, dCTP, dGTP, and dUTP; 16 μl each of DM152 (1.5 μM) and DM151 (1.5 μM); 16 μl of AW109 cRNA template (5×10³ copies/μl); and 16 μl of rTth (2.5 units/μ 1). The final volume was 144 μl (18 μl/reaction). A 7X PCR master mixture was prepared that contained: 297 μl sterile DEPC-treated distilled water, 56 μl 10X PCR buffer (100 mM Tris-HCl, pH 8.3; 1M KCl; 7.5 mM EGTA; 50% glycerol [v/v]); 140 μl 10 mM MgCl₂; 56 μl dNTP mix containing 2 mM each of dATP, dCTP, dGTP, dUTP; 5.6 μl of each of DM152 and DM151 (15 μM). The final volume was 560 μl, 80 μl per reaction.

Eighteen μl of the RT mix was aliquoted into six sterile microcentrifuge tubes and MnCl₂ added in a 2 μl volume to provide a final MnCl₂ concentration as follows: Tube Nos. 1 and 2 (1.2 mM MnCl₂); Tube Nos. 3 and 4 (1.0 mM MnCl₂); and Tube Nos. 5 and 6 (0.8 mM MnCl₂). A mineral oil overlay (75 μl) was added to each tube and the reactions were incubated at 70° C. for 15' in a water bath. Following the 70° C. incubation, 80 μl of the PCR master mix was added to each. The reaction tubes were thermocycled as follows: 2 minutes at 95° C. for 1 cycle; 1 minute at 95° C. and 1 minute at 60° C. for 35 cycles; 7 minutes at 60° C. for 1 cycle; and soak at 4° C.

Results

Five μl of each reaction mix was electrophoresed on a 2% NuSieve 1 % agarose gel. The gel was stained and photographed. PCR product of the expected size was clearly visible in samples from all three MnCl₂ concentrations. The product yield increased with increasing MnCl₂ concentration.

EXAMPLE XII

Procedure for Sterilization of a Homogeneous RT/PCR Assay

This example illustrates a method for sterilization of a homogeneous RT/PCR reaction contaminated with nucleic acids generated from a previous reaction. The reaction mix is treated with UNG prior to reverse transcription.

The unconventional nucleotide, dUTP, is incorporated during the RT/PCR reaction. Consequently, any product DNA present as a contaminant in subsequent reactions can be hydrolyzed using UNG.

In a 0.2 ml MicroAmp ® tube combine 5.5 μl sterile distilled water; 2 μl 10X RT buffer (100 mM Tris-HCl, pH 8.3; 900 mM KCl); 2 μl of 8 μM MnCl₂; 2 μl dNTP mix containing 2 mM each of dATP, dCTP, dGTP, and dUTP; 2 μl each of DM152 (1.5 μM) and DM151 (1.5 μM); 2 μl of AW109 cRNA template 5×10³ copies/μl); 0.5 μl UNG (1 unit/μl); and 2 μl of rTth (2.5 units/μl). The reaction is incubated for 10 minutes at room temperature and subsequently heated at 70° C. for 15 minutes to denature the glycosylase prior to reverse transcription. The cDNA is then amplified by a PCR.

In this example, the positive control RNA serves as a template for DM152 and DM151 is the upstream primer. The total reaction volume is 20 μl/sample. Incubate the tubes in a Thermal Cycler (for example, PECI TC 9600) as follows:

70° C. for 15 minutes for 1 cycle
95° C. for 15 seconds and 60° for 20 seconds for 2 cycles
90° C. for 15 seconds and 60° C. for 20 seconds for 33 cycles
60° C. for 4 minutes for I cycle The optimal manganese concentration may vary depending on the particular sample, target, primers, and the dNTP concentration in the reaction mixture.

Deposition of Cultures

The cultures were deposited in the Cetus Master Culture Collection (CMCC), 1400 Fifty-Third Street, Emeryville, Calif. 94608, USA, and accepted by the American Type Culture Collection (ATCC), 12301 Parklawn Drive, Rockville, Md., USA. The CMCC and ATCC accession numbers and ATCC deposit dates for the deposited samples are given below:

| Culture | ATCC No. | Deposit Date |
| --- | --- | --- |
| pBSM:Tth10 | 68195 | 12/21/89 |
| pAW109 | 68125 | 10/27/89 |

These deposits were made under the Budapest Treaty on the International Recognition of the Deposit of Microorganisms for the Purpose of (Budapest Treaty). This assures maintenance of a viable culture for 30 years from date of deposit. The deposits will be made available by ATCC under the terms of the Budapest treaty, and subject to an agreement between applicants and ATCC which assures permanent and unrestricted availability upon issuance of the pertinent U.S. patent The Assignee herein agrees that if the culture on deposit should die or be lost or destroyed when cultivated under suitable conditions, it will be promptly replaced upon notification with a viable specimen of the same culture. Availability of the deposits is not to be construed as a license to practice the invention in contravention of the rights granted under the authority of any government in accordance with its patent laws.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

The invention has been described in detail, but it will be understood that variations and modifications can be effected within the spirit and scope of the following claims.

We claim:

1. A homogeneous single addition method for copying a target RNA molecule in a sample to produce a cDNA, and then amplifying the resulting cDNA, the method comprising the steps of:

(a) treating said sample in a reaction mixture comprising a first and second primer, wherein said first primer is sufficiently complementary to said target RNA to hybridize therewith and initiate synthesis of a cDNA molecule complementary to said target RNA, and said second primer is sufficiently homologous to said target RNA to hybridize to said cDNA and initiate synthesis of an extension product, and a thermostable DNA polymerase having reverse transcriptase activity in the presence of all four deoxyribonucleoside triphosphates, in an appropriate buffer, wherein said buffer comprises $Mn^{+2}$, at a temperature sufficient for said thermostable DNA polymerase to initiate synthesis of an extension product of said first primer to provide a cDNA molecule complementary to said target RNA;

(b) treating said reaction mixture at an appropriate temperature to provide single-stranded cDNA;

(c) treating said reaction mixture at an appropriate temperature for said thermostable DNA polymerase to initiate synthesis of an extension product of said second primer to provide a double-stranded cDNA molecule; and (d) amplifying the double-stranded cDNA molecule of step (c) by a polymerase chain reaction.

2. The method of claim 1 wherein said thermostable DNA polymerase is the *Thermus aquaticus* DNA polymerase or the *Thermus thermophilus* DNA polymerase.

3. The method of claim 2 wherein said DNA polymerase is recombinant Tth DNA polymerase.

4. The method of claim 1 wherein said sample comprises between 0.1 picograms and 1 microgram of RNA.

5. The method of claim 4 wherein said sample comprises between 1 and $10^8$ copies of said target RNA.

6. The method of claim 1 wherein the temperature at step (a) is between 40° C. and 80° C.

7. The method of claim 1 wherein said target RNA molecule is diagnostic of a genetic or infectious disease.

* * * * *